(12) United States Patent
Bassani et al.

(10) Patent No.: US 7,956,623 B2
(45) Date of Patent: Jun. 7, 2011

(54) CONTAINER FILLING MACHINE

(75) Inventors: Loris Bassani, Montreal (CA);
Gueorgui Poklitar, Montreal (CA)

(73) Assignee: Countlab, Inc, Montreal-Nord, Quebec (CA)

( * ) Notice: Subject to any disclaimer, the term of this patent is extended or adjusted under 35 U.S.C. 154(b) by 0 days.

(21) Appl. No.: 12/094,949

(22) PCT Filed: Feb. 16, 2007

(86) PCT No.: PCT/CA2007/000238
§ 371 (c)(1),
(2), (4) Date: Oct. 7, 2008

(87) PCT Pub. No.: WO2008/098340
PCT Pub. Date: Aug. 21, 2008

(65) Prior Publication Data
US 2009/0039899 A1    Feb. 12, 2009

(51) Int. Cl.
*G01R 27/26* (2006.01)
*B65G 51/36* (2006.01)
(52) U.S. Cl. ........ 324/663; 324/672; 324/679; 324/686; 406/34
(58) Field of Classification Search ............... 324/663, 324/672, 679, 686, 222, 600; 406/34
See application file for complete search history.

(56) References Cited

U.S. PATENT DOCUMENTS

| | | |
|---|---|---|
| 1,383,623 A | 7/1921 | Groves |
| 2,845,759 A | 8/1958 | Cote et al. |
| 3,028,713 A | 4/1962 | Kennedy et al. |
| 3,081,588 A | 3/1963 | Klapes et al. |
| 3,139,713 A | 7/1964 | Merrill et al. |
| 3,677,437 A | 7/1972 | Haigler |
| 3,746,211 A | 7/1973 | Burgess, Jr. |
| 3,925,960 A | 12/1975 | Saari et al. |
| 4,408,295 A | 10/1983 | Kavage et al. |
| 4,461,363 A * | 7/1984 | Loy .................................. 177/1 |

(Continued)

FOREIGN PATENT DOCUMENTS

CA       2060784 A1     8/1992

(Continued)

OTHER PUBLICATIONS

International Search Report and Written Opinion issued in PCT/CA2007/000238, dated Nov. 9, 2007, 17 pages.

*Primary Examiner* — Melissa J Koval
*Assistant Examiner* — Farhana Hoque
(74) *Attorney, Agent, or Firm* — Senniger Powers LLP

(57) ABSTRACT

The present invention provides a container filling machine comprising a sensing device for detecting the integrity of discrete articles for personal treatment to be packaged in a container. The sensing device comprises a pair of capacitor plates positioned in a substantially opposing relationship for creating therebetween an electric field, a track for guiding the discrete articles for personal treatment through said electric field and a processing unit. The processing unit is in communication with the pair of capacitor plates, and is operative for detecting a change in capacitance as a discrete article passes through the electric field in order to determine the integrity of the discrete article on the basis of the change in capacitance and a characteristic capacitance change signature. The container filling machine further comprises a transportation device, a rejection device, a counting device and a plurality of path blocking devices.

48 Claims, 12 Drawing Sheets

U.S. PATENT DOCUMENTS

| | | |
|---|---|---|
| 4,680,464 A | 7/1987 | Bross |
| 4,922,181 A | 5/1990 | Pullan |
| 4,924,955 A * | 5/1990 | Dauge ............... 177/210 C |
| 4,932,559 A | 6/1990 | Stein |
| 4,943,227 A | 7/1990 | Facchini |
| 5,200,013 A | 4/1993 | Traber |
| 5,238,124 A | 8/1993 | Cane et al. |
| 5,333,778 A | 8/1994 | Specker |
| 5,439,036 A | 8/1995 | Krämer |
| 5,463,839 A | 11/1995 | Stange et al. |
| 5,489,019 A | 2/1996 | DiNanno et al. |
| 5,585,732 A | 12/1996 | Steele et al. |
| 5,596,865 A | 1/1997 | Krämer |
| 5,737,902 A | 4/1998 | Aylward |
| 5,931,286 A | 8/1999 | Illi |
| 5,950,404 A | 9/1999 | Meyer et al. |
| 6,185,901 B1 | 2/2001 | Aylward |
| 6,266,946 B1 | 7/2001 | Aylward |
| 6,269,612 B1 | 8/2001 | Aylward |
| 6,401,429 B2 | 6/2002 | Aylward |
| 6,494,022 B1 | 12/2002 | Aylward |
| 6,504,387 B1 * | 1/2003 | Shail et al. ............... 324/690 |
| 6,505,460 B2 | 1/2003 | Aylward |
| 6,625,955 B2 | 9/2003 | Aylward |
| 6,640,842 B1 | 11/2003 | Laukenmann et al. |
| 6,681,550 B1 | 1/2004 | Aylward |
| 6,755,008 B2 | 6/2004 | Schmetzer et al. |
| 6,789,780 B2 | 9/2004 | Pieri |
| 6,799,413 B2 | 10/2004 | Aylward |
| 6,925,782 B2 | 8/2005 | Aylward |
| 6,929,115 B2 | 8/2005 | Monti |
| 6,932,210 B2 | 8/2005 | Krämer |
| 6,971,216 B2 | 12/2005 | Monti |
| 7,007,821 B2 | 3/2006 | Aylward |
| 7,025,207 B2 | 4/2006 | Breu et al. |
| 7,121,410 B2 | 10/2006 | Rohrmus et al. |
| 7,331,540 B2 | 2/2008 | Klaumünzner |
| 2001/0045081 A1 | 11/2001 | Aylward |
| 2002/0023414 A1 | 2/2002 | Aylward |
| 2002/0108356 A1 | 8/2002 | Aylward |
| 2002/0166790 A1 | 11/2002 | Aylward |
| 2002/0194815 A1 | 12/2002 | Aylward |
| 2004/0007442 A1 | 1/2004 | Monti |
| 2004/0035878 A1 | 2/2004 | Aylward |
| 2004/0123560 A1 | 7/2004 | Monti |
| 2004/0123561 A1 | 7/2004 | Monti |
| 2004/0128955 A1 | 7/2004 | Aylward |
| 2004/0139695 A1 | 7/2004 | Monti |
| 2005/0000192 A1 | 1/2005 | Aylward |
| 2005/0007588 A1 | 1/2005 | Tarozzi et al. |
| 2005/0077313 A1 | 4/2005 | Aylward |
| 2005/0189373 A1 | 9/2005 | Aylward |
| 2005/0217208 A1 * | 10/2005 | Cicognani ............... 53/54 |
| 2005/0230001 A1 | 10/2005 | Monti |

FOREIGN PATENT DOCUMENTS

| | | |
|---|---|---|
| CA | 2321725 A1 | 9/1999 |
| DE | 4118878 A1 | 1/1993 |
| DE | 4331879 A1 | 3/1994 |
| DE | 202004008975 U1 | 9/2004 |
| DE | 102004027590 B3 | 11/2005 |
| EP | 0259354 A1 | 3/1988 |
| EP | 0347392 A1 | 12/1989 |
| EP | 0360765 A1 | 3/1990 |
| EP | 0486439 A1 | 5/1992 |
| EP | 0491658 A1 | 6/1992 |
| EP | 0499577 A1 | 8/1992 |
| EP | 0561737 A1 | 9/1993 |
| EP | 0588838 A1 | 3/1994 |
| EP | 0588993 A1 | 3/1994 |
| EP | 0499577 B1 | 9/1994 |
| EP | 0618447 A2 | 10/1994 |
| EP | 0630816 A2 | 12/1994 |
| EP | 0561737 B1 | 1/1995 |
| EP | 0588993 B1 | 1/1995 |
| EP | 0639528 A1 | 2/1995 |
| EP | 0588838 B1 | 9/1995 |
| EP | 0677482 A1 | 10/1995 |
| EP | 0770554 A1 | 5/1997 |
| EP | 0816235 A1 | 1/1998 |
| EP | 0618447 B1 | 5/1998 |
| EP | 0932554 A1 | 8/1999 |
| EP | 0816235 B1 | 4/2000 |
| EP | 1060362 A1 | 12/2000 |
| EP | 1061361 A1 | 12/2000 |
| EP | 1106511 A1 | 6/2001 |
| EP | 1171347 A1 | 1/2002 |
| EP | 1221410 A2 | 7/2002 |
| EP | 1251073 A1 | 10/2002 |
| EP | 1270441 A1 | 1/2003 |
| EP | 1041022 B1 | 6/2003 |
| EP | 1171347 B1 | 1/2004 |
| EP | 1380510 A1 | 1/2004 |
| EP | 1389583 A1 | 2/2004 |
| EP | 1391386 A2 | 2/2004 |
| EP | 1052202 B1 | 3/2004 |
| EP | 1395500 A1 | 3/2004 |
| EP | 1413517 A1 | 4/2004 |
| EP | 1060362 B1 | 5/2004 |
| EP | 1043252 B1 | 6/2004 |
| EP | 1431180 A1 | 6/2004 |
| EP | 1431181 A1 | 6/2004 |
| EP | 1431182 A2 | 6/2004 |
| EP | 1471993 A1 | 11/2004 |
| EP | 1481913 A1 | 12/2004 |
| EP | 1253095 B1 | 9/2005 |
| EP | 1380510 B1 | 9/2005 |
| EP | 1588944 A1 | 10/2005 |
| EP | 1602593 A1 | 12/2005 |
| GB | 2270771 A | 3/1994 |
| GB | 2310729 A | 3/1997 |
| GB | 2326488 A | 12/1998 |
| JP | 1210200 A | 8/1989 |
| JP | 4352669 A | 12/1992 |
| JP | 5228447 A | 9/1993 |
| JP | 6032347 A | 2/1994 |
| JP | 2000079912 A | 3/2000 |
| JP | 2002249103 A | 9/2002 |
| WO | 8704407 A1 | 7/1987 |
| WO | 9222278 A1 | 12/1992 |
| WO | 9222401 A1 | 12/1992 |
| WO | 9509452 A1 | 4/1995 |
| WO | 9625333 A1 | 8/1996 |
| WO | 9626873 A1 | 9/1996 |
| WO | 9701489 A1 | 1/1997 |
| WO | 9706061 A1 | 2/1997 |
| WO | 9719010 A1 | 5/1997 |
| WO | 9815461 A1 | 4/1998 |
| WO | 9857144 A1 | 12/1998 |
| WO | 9945343 A1 | 9/1999 |
| WO | 9962699 A1 | 12/1999 |
| WO | 0064744 A1 | 11/2000 |
| WO | 02100736 A1 | 12/2002 |
| WO | 03097459 A2 | 11/2003 |
| WO | 2005023672 A1 | 3/2005 |

* cited by examiner

CONTAINER FILLING MACHINE

FIELD OF THE INVENTION

The present invention relates to container filling machines, and specifically to container filling machines for assessing and discarding defective discrete articles for personal treatment, such as pharmaceutical pills.

BACKGROUND OF THE INVENTION

Packaging machines for filling containers with discrete articles for personal treatment, such as pharmaceutical pills, are known in the art. However, existing container filling machines are plagued with numerous deficiencies that often render them ineffective and inefficient.

The purpose of container filling machines for discrete articles for personal treatment is to take a large supply of such discrete articles and to transport them towards a container, while ensuring that a desired number of the discrete articles for personal treatment are placed into the container. Many container filling machines are also operative for detecting the integrity of the discrete articles for personal treatment so that defective discrete articles for personal treatment are not included in the containers.

A first deficiency with existing container filling machines for packaging discrete articles for personal treatment is that they use vibrating trays in order to space the discrete articles from each other and move them towards one or more sensing devices, and ultimately towards the containers. However, these vibrating trays do not evenly space and distribute the discrete articles for personal treatment as they move towards the sensing devices that are operative to detect the integrity of the discrete articles. As such, in some cases, two or more discrete articles for personal treatment are provided to the sensing device at the same time, which can cause incorrect readings.

A second deficiency with many existing container filling machines is that they use optical sensors in order to determine the integrity of each discrete article for personal treatment. Such optical sensors take an optical scan of the exterior shape of the discrete article for personal treatment as it passes in front of one or more optical cameras. The optical cameras then determine the integrity of the discrete article for personal treatment based on the optical scan. While such optical sensors can detect the integrity of most discrete articles for personal treatment, depending on the orientation of the discrete article for personal treatment as it passes by the optical cameras, the optical scan may not detect a defective region of the discrete article. In addition, if two discrete articles for personal treatment pass through the optical scanner at the same time, the optical cameras will be unable to detect the integrity of one or both of the discrete articles for personal treatment.

In addition, the manner in which many existing container filling machines detect whether there exists one or more defective discrete articles for personal treatment in a container is to weigh the container once the container has been filled. In the case where the container does not weigh a predetermined correct weight, then it is determined that the container contains one or more defective discrete articles for personal treatment and the entire container is emptied and then re-filled. It can be appreciated that this is both inefficient, and causes a lot of wasted discrete articles for personal treatment.

In light of the above, there is a need in the industry for an improved container filling machine that alleviates, at least in part, the deficiencies of existing container filling machines, and container filling machine systems.

SUMMARY OF THE INVENTION

In accordance with a first broad aspect, the present invention provides a device for carrying discrete articles for personal treatment from a pick-up location to a drop-off location. The device is suitable for use in container filling machines for placing the discrete articles for personal treatment into containers such as bottles. The device comprises a moving surface comprising a plurality of spaced apart air passageways arranged according to a pattern and a vacuum device for suctioning air through the plurality of spaced apart air passageways such that a discrete article located in proximity to a pick-up location of the moving surface is suctioned to an air passageway of the moving surface. The suctioned article is transported by the moving surface to a drop-off location where the discrete articles for personal treatment are no longer transported by the moving surface.

In accordance with a second broad aspect, the present invention provides a method for carrying discrete articles for personal treatment from a pick-up location to a drop-off location. The method comprises providing a moving surface having a plurality of spaced apart air passageways arranged according to a pattern, suctioning air through the plurality of spaced apart air passageways such that discrete articles for personal treatment located at a pick-up location are suctioned to respective ones of the spaced apart air passageways and releasing the discrete articles for personal treatment from the moving surface at the drop-off location such that the discrete articles for personal treatment are no longer transported by the moving surface.

In accordance with a third broad aspect, the present invention provides a container filling machine for bottling discrete articles for personal treatment. The container filling machine comprises a transportation device suitable for carrying discrete articles for personal treatment from a pick-up location to a drop-off location and a sensing device suitable for determining the integrity of the discrete articles for personal treatment that are released at the drop-off location. The transportation device comprises a moving surface comprising a plurality of spaced apart air passageways arranged according to a predetermined pattern and a vacuum device for suctioning air through the plurality of spaced apart air passageways, such that a discrete article for personal treatment located in proximity to a pick-up location of the moving surface is suctioned to a respective one of the air passageways of the moving surface. The suctioned article is carried by the moving surface to a drop-off location wherein the article is no longer transported by the moving surface. The sensing device comprises at least one capacitor through which articles released at the drop-off location travel and a processing unit. The processing unit is operative for determining a change in capacitance at the at least one capacitor as a discrete article passes therethrough and determining at least in part on the basis of the change in capacitance if the discrete article is integral.

In accordance with a fourth broad aspect, the present invention provides a sensing device suitable for use with a container filling machine for detecting the integrity of discrete articles for personal treatment to be placed in a container. The sensing device comprises a pair of capacitor plates positioned in a substantially opposing relationship for creating therebetween an electric field, a track for guiding the discrete articles for personal treatment through said electric field and a processing unit. The track preventing the discrete articles for personal treatment from tumbling during travel through said electric field. The processing unit is in communication with the pair of capacitor plates, and is operative for detecting a change in capacitance as a discrete article passes through the electric field and determining the integrity of the discrete article at least in part on the basis of the change in capacitance.

In accordance with a fifth broad aspect, the invention provides a sensing device suitable for use with a container filling machine. The sensing device is operative for detecting the integrity of discrete articles for personal treatment to be loaded in a container. The sensing device comprises a measurement capacitor, a reference capacitor and a processing unit in communication with the measurement capacitor and the reference capacitor. The processing unit is operative for detecting a difference in capacitance change between the measurement capacitor and the reference capacitor as a discrete article passes through the measurement capacitor and determining the integrity of the discrete article at least in part on the basis of the difference in capacitance change.

In accordance with a sixth broad aspect, the present invention provides a method for detecting the integrity of discrete articles for personal treatment to be loaded in a container. The method comprises providing a measurement capacitor, providing a reference capacitor, detecting a difference in capacitance change between the measurement capacitor and the reference capacitor when a discrete article for personal treatment passes through the measurement capacitor and determining the integrity of the discrete article at least in part on the basis of the difference in capacitance change.

In accordance with a seventh broad aspect, the present invention provides a sensing device suitable for use with a container filling machine for detecting the integrity of discrete articles for personal treatment to be loaded in a container. The sensing device comprises a pair of capacitor plates and a processing unit. The pair of capacitor plates are positioned in a substantially opposing relationship for creating therebetween an electric field in response to voltage impressed across the plates which is less than 100V. The processing unit is in communication with the pair of capacitor plates and is operative for detecting a change in capacitance as a discrete article for personal treatment passes through the electric field and for determining the integrity of the discrete article on the basis of the change in capacitance.

In accordance with an eighth broad aspect, the present invention provides a container filling machine for loading discrete articles for personal treatment into a container. The container filling machine defines a path along which the discrete articles for personal treatment travel towards a container. The container filling machine comprises a sensing device suitable for detecting the integrity of a discrete article for personal treatment, a rejection device positioned between the sensing device and a container and a processing unit in communication with the sensing device and the rejection device. Upon detection at the sensing device of a defective discrete article, the processing unit is operative for causing the rejection device to remove the defective discrete article from continued travel along the path towards the container.

In accordance with a ninth broad aspect, the present invention provides a container filling machine for bottling discrete articles for personal treatment. The container filling machine includes at least two paths for feeding discrete articles for personal treatment into a container and comprises a counting device for counting the discrete articles for personal treatment travelling along each path, and a path blocking device associated to each respective path. Each path blocking device is capable of moving between a first position and a second position, wherein in the first position the discrete articles for personal treatment are able to enter a container, and in the second position the discrete articles for personal treatment are prevented from entering into the container. The container filling machine further comprises a processing unit in communication with each path blocking device. The processing unit is operative for causing each path blocking device to move between the first position and the second position at least in part on the basis of information received from a corresponding counting device.

These and other aspects and features of the present invention will now become apparent to those of ordinary skill in the art upon review of the following description of specific embodiments of the invention and the accompanying drawings.

Other aspects and features of the present invention will become apparent to those ordinarily skilled in the art upon review of the following description of specific embodiments of the invention in conjunction with the accompanying figures.

DETAILED DESCRIPTION

Overall Machine

Figure 1:
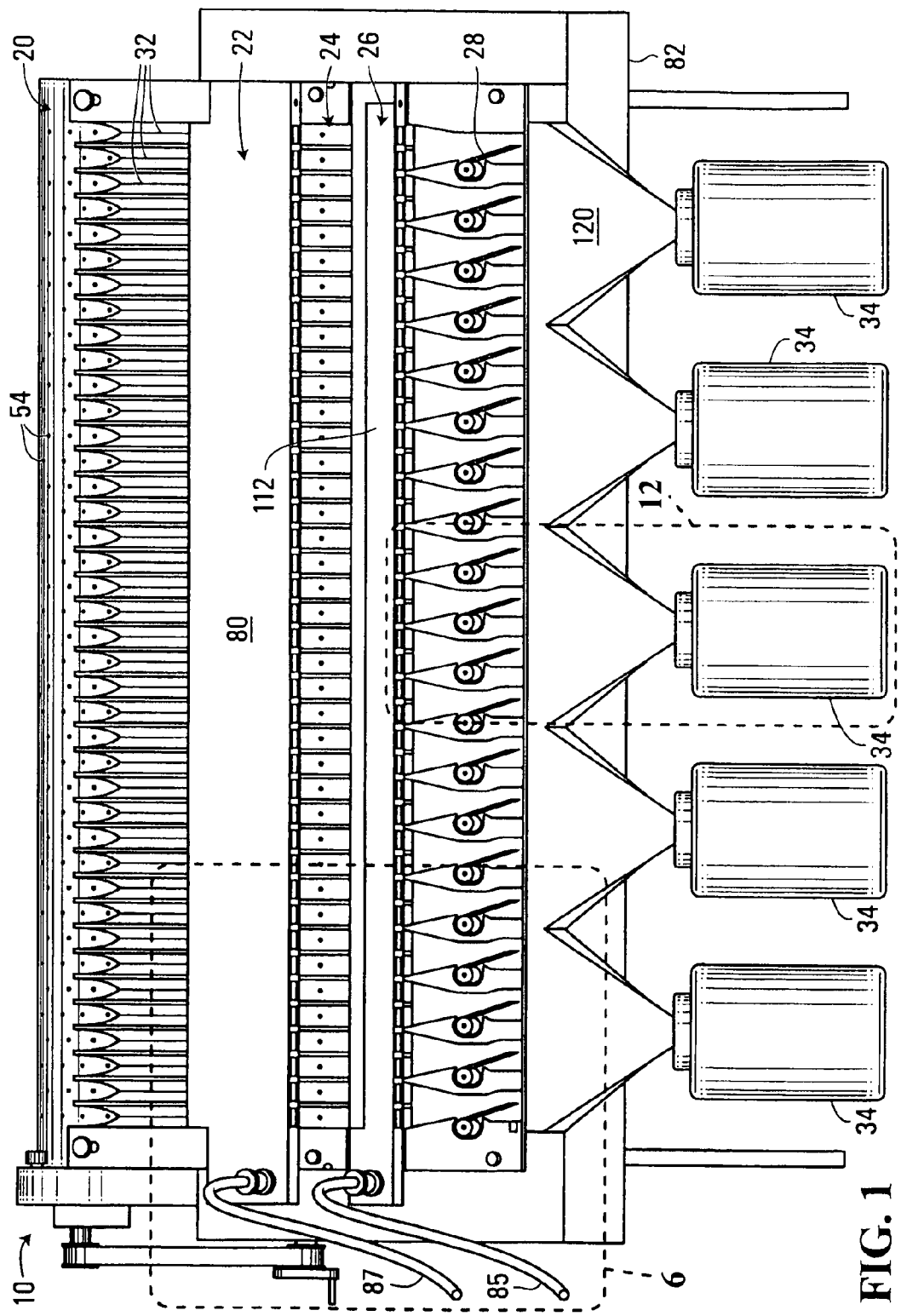
FIG. 1 shows a front representational view of a container filling machine in accordance with a non-limiting example of implementation of the present invention.
Figure 2:
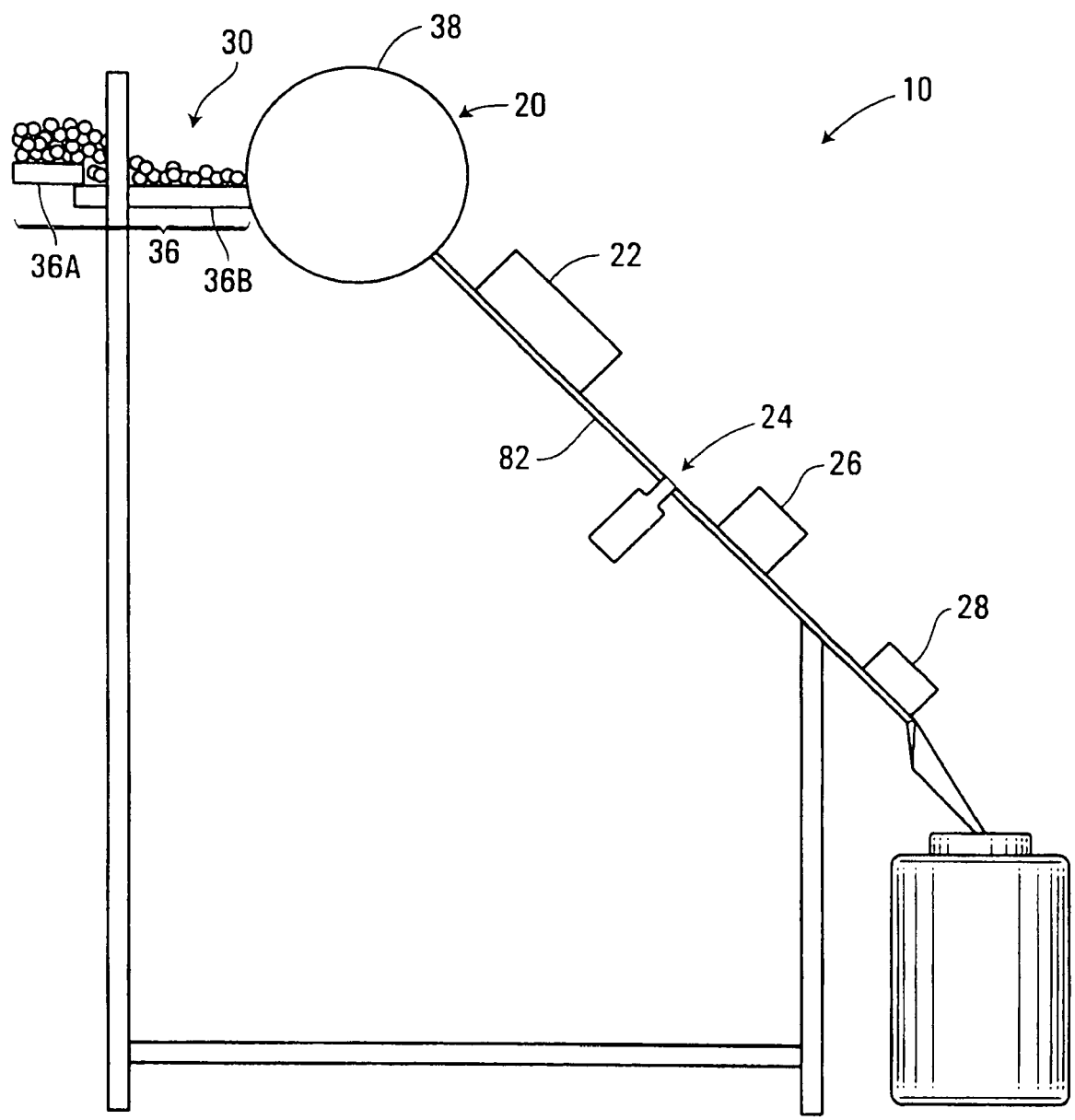
FIG. 2 shows a side representational view of the container filling machine of FIG. 1.

Shown in FIGS. 1 and 2 is a container filling machine 10 in accordance with a non-limiting example of implementation of the present invention. More specifically, FIG. 1 shows a front view of the container filling machine 10, and FIG. 2 shows a side view of the container filling machine 10. The container filling machine 10 is suitable for loading into containers any discrete articles for personal treatment, such as pharmaceutical discrete articles, cosmetic items, etc. . . . . . As used herein, the term "discrete article for personal treatment" includes any type of pharmaceutical discrete article for personal treatment that can be ingested (such as pressed-powder or gel cap pills, among other possibilities) as well as any cosmetic item that can be applied to an external part of the body (such as moisturiser capsules, for example).

In the non-limiting embodiment shown, the container filling machine 10 includes a transportation device 20, a sensing device 22, one or more rejection devices 24, a counting device 26, and a series of path blocking devices 28, which will each be described in more detail throughout the present application. The transportation device 20 is operative for transporting the discrete articles for personal treatment from an initial loading location 30 (shown in FIG. 2) towards a plurality of paths 32. More specifically, the transportation device 20 delivers the discrete articles for personal treatment from the initial loading location 30 to the plurality of paths 32 in accordance with a predetermined pattern, such that the discrete articles for personal treatment are provided to the paths 32 in a predictable spaced-apart manner.

Once deposited onto a path 32, each discrete article for personal treatment travels through the sensing device 22. The sensing device 22 is operative for assessing the integrity of each discrete article for personal treatment on a individual basis. In the case where a discrete article for personal treatment is found to be defective by the sensing device 22, the rejection device 24 then removes the defective discrete article from continued travel along its path 32. As such, any defective discrete articles for personal treatment are removed from continued travel towards a container 34. In the case where a discrete article for personal treatment is not defective, it continues along its path 32 towards the counting device 26 and one of the series of path blocking devices 28, prior to entering a container 34. The counting device 26 is operative for counting the number of integral discrete articles for personal treatment that pass therethrough, such that the path blocking devices 28 can control the number of discrete articles for personal treatment that enter each container 34. In this manner, the container filling machine 10 is able to fill a plurality of containers 34 with an exact number of integral discrete articles for personal treatment. The path blocking devices 28 further permit the container filling machine 10 to keep a steady flow of discrete articles for personal treatment travelling towards the containers 34, even as filled containers 34 are being replaced by empty containers.

Once filled, the containers 34 continue towards other machines that put caps on the containers 34, apply labels to the containers 34, and generally perform any other operation on the containers 34 that is required prior to providing the containers 34 to an end consumer.

Figure 3:
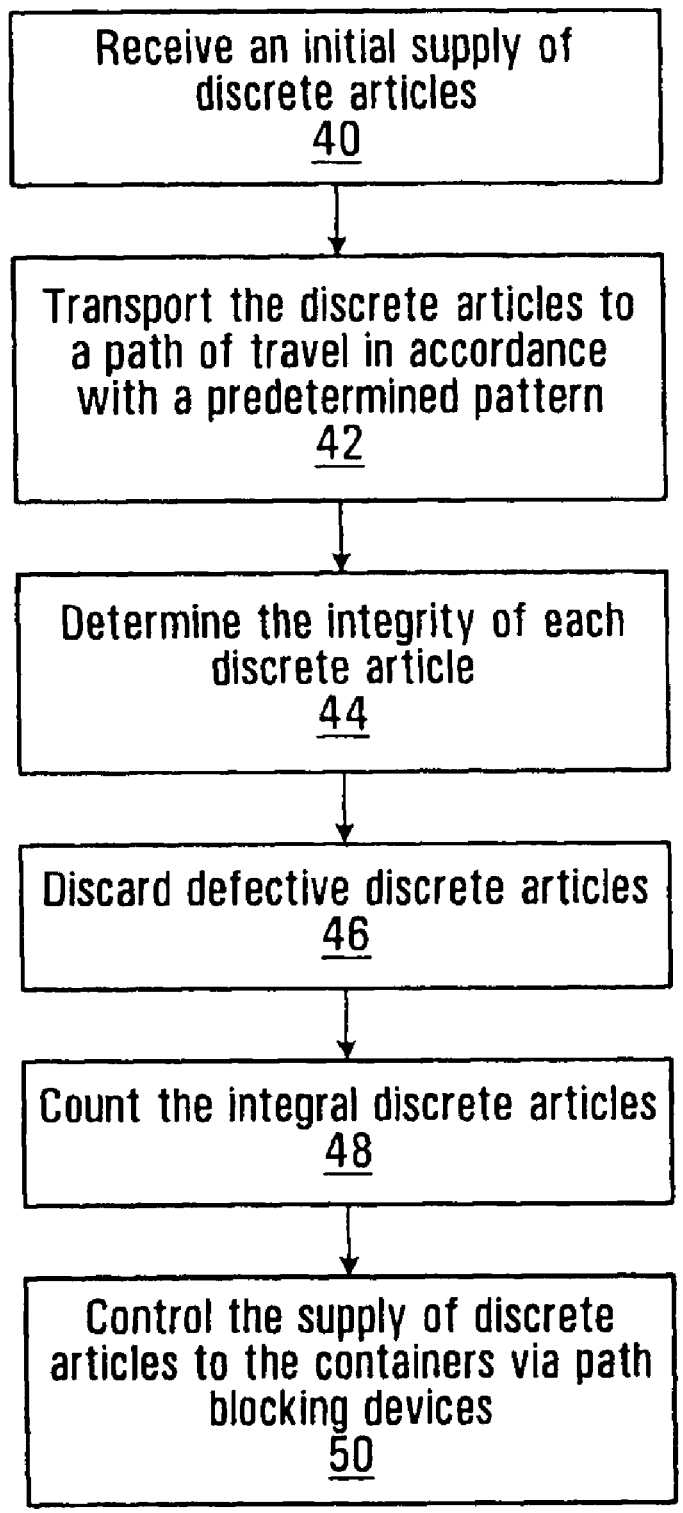
FIG. 3 shows a non-limiting flow diagram of the operation of the container filling machine of FIG. 1 in accordance with an example of implementation of the present invention.

Shown in FIG. 3, is a non-limiting flow diagram of the overall operation of the container filling machine 10. At step 40, the container filling machine 10 receives an initial supply of discrete articles for personal treatment that are provided to the machine 10 in a disorganised fashion. For example, the supply of discrete articles for personal treatment may simply be poured into an initial loading location 30 from another container. At step 42, the transportation device 20 transports the discrete articles for personal treatment from the initial loading location 30 to a path of travel 32 in accordance with a predetermined pattern. At step 44, the discrete articles for personal treatment pass through the sensing device 22, such that the sensing device 22 can determine the integrity of each of the discrete articles for personal treatment that passes therethrough. In this manner, any defective discrete articles for personal treatment are identified. At step 46, any defective discrete articles for personal treatment that were identified by the sensing device 22 are discarded by the rejection device 24, such that they are removed from their path 32 and no longer continue travelling towards a container 34. At step 48, the counting device 26 counts the integral discrete articles for personal treatment that remain on a path 32 towards a container 34. Finally, at step 50, the container filling machine 10 controls the supply of discrete articles for personal treatment to the containers 34 via the path blocking devices 28.

It should be appreciated that numerous discrete articles for personal treatment may be travelling on the paths 32 at the same time, such that once the discrete articles for personal treatment are flowing through the machine, each of the steps described above is performed at substantially the same time. For example, while the transportation device 20 is transporting certain discrete articles for personal treatment, the sensing device 22 may be sensing other discrete articles for personal treatment that are further on in their travel towards a container 34, and the counting device 26 may be counting discrete articles for personal treatment that are still further on in their travel towards a container 34.

In some embodiments of the invention, all or part of the functionality that will be described below in relation to each of the transportation device 20, the sensing device 22, the rejection devices 24, the counting device 26 and the path blocking devices 28, may be implemented as pre-programmed hardware or firmware elements (e.g., application specific integrated circuits (ASICs), electrically erasable programmable read-only memories (EEPROMs), etc.) or other related components.

However, in a preferred embodiment, the functionality of the transportation device 20, the sensing device 22, the rejection devices 24, the counting device 26 and the path blocking devices 28 is controlled via at least one software driven processing unit.

Figure 4:
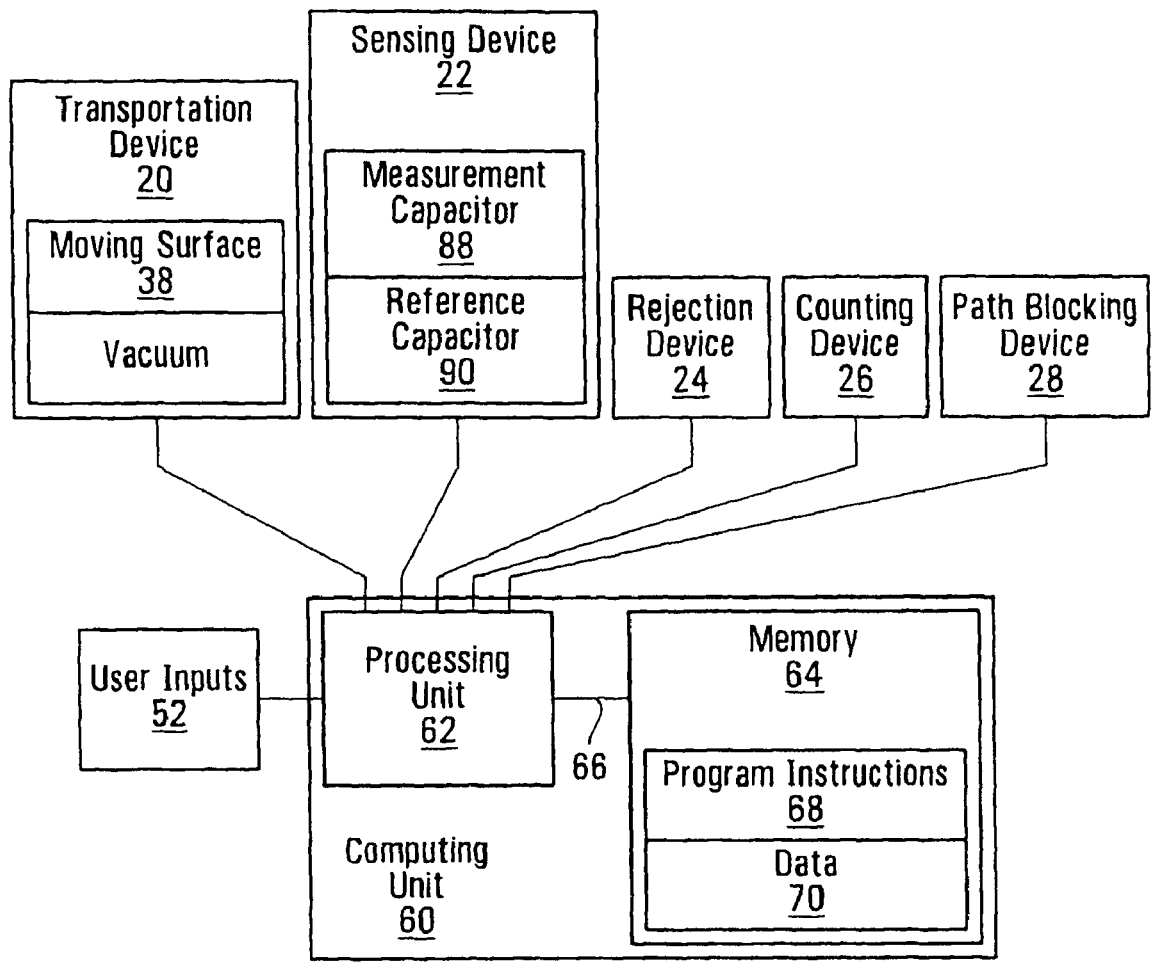
FIG. 4 shows a non-limiting block diagram of a computing unit suitable for implementing the functionality of the container filling machine of FIG. 1.

Shown in FIG. 4 is a non-limiting block diagram of a computing unit 60 suitable for controlling the different components of the container filling machine 10. As shown, the computing unit 60 includes a processing unit 62 and a memory unit 64 that are in communication with each other via a communication bus 66. The memory unit 64 includes program instructions 68 and data 70 that are accessed and processed by the processing unit 62, such that the processing unit 62 can control the functionality and operations of the components of the container filling machine 10. As shown, the processing unit 62 is in communication with the transportation device 20, the sensing device 22, the rejection device 24, the counting device 26 and the path blocking devices 28. The processing unit 62 is also in communication with user inputs 52 that enable the user to enter commands and/or data into the computing unit 60, In this non-limiting embodiment, all or part of the functionality of the transportation device 20, the sensing device 22, the rejection device 24, the counting device 26 and the path blocking devices 28 may be implemented as software consisting of a series of instructions for execution by the processing unit 62. For example, the series of instructions could be stored in the memory 64, which could be a medium which is fixed, tangible and readable directly by the processing unit 62 (e.g., removable diskette, RAM, flash memory, CD-ROM, ROM, PROM, EEPROM or fixed disk).

The computing unit 60 may comprise a number of interfaces for receiving or sending data elements to external devices. For example, the computing unit 60 includes an interface (not shown) for receiving signals from the user inputs 52. These user inputs may allow an operator of the container filling machine 10 to enter commands and parameters for programming and/or controlling the different components of the container filling machine 10. This may be done in order to change operational settings of the different components, and/or to enter specific data, such as a desired operating speed, the number of discrete articles for personal treatment per container, etc. . . . . The computing unit 60 may further include an interface for releasing data to be displayed to a user on a display (not shown).

It should be appreciated that the functionality of some of the components of the container filling machine 10 is directly dependent on events that occur at other components of the container filling machine 10. For example, the operation of the rejection device 24 is dependent on the detection at the sensing device 22 of a defective discrete article for personal treatment. Likewise, the operation of the path blocking devices 28 is at least partly dependent on the number of discrete articles for personal treatment counted by the counting device 26. As such, it is advantageous to have a single processing unit 62 in communication with each of the components (transportation device 20, the sensing device 22, the rejection devices 24, the counting device 26 and the path blocking devices 28) such that the processing unit 62 can co-ordinate the operation of the different components.

However, in accordance with an alternative example of implementation, the transportation device 20, the sensing device 22, the rejection devices 24, the counting device 26 and the path blocking devices 28 may each include their own separate processing unit (not shown). In such an embodiment, at least some of the processing units would be in communication with each other over a communication link, so as to co-ordinate the functionality of the different components. More specifically, the processing unit for the sensing device 22 would need to issue a signal to the processing unit of the rejection device 24 upon detection of a defective discrete article for personal treatment, such that the processing unit for the rejection device 24 could cause the rejection device 24 to remove the defective discrete article for personal treatment from its path of travel.

The operation and functionality of the transportation device 20, the sensing device 22, the rejection device 24, the counting device 26, and the path blocking devices 28 will now be described in more detail hereinbelow.

Transportation Device 20

As described above, the transportation device 20 is operative for receiving an initial load of discrete articles for personal treatment, and for releasing those discrete articles for personal treatment at a drop-off location in accordance with a predetermined pattern. As shown in FIG. 2, an initial load of discrete articles for personal treatment is placed into the container filling machine 10 at an initial loading position 30. At the initial loading position 30, the discrete articles for personal treatment do not need to be in any particular order or orientation, and as such can be quickly dumped into the container filling machine 10. This can be done either manually by an operator of the machine 10, or mechanically by a different machine.

In accordance with a non-limiting example of implementation, the initial loading position 30 includes a pair of vibrating trays 36a and 36b that cause the discrete articles for personal treatment to approach a moving surface 38. Although only two vibrating trays 36a and 36b are shown in FIG. 2, it should be appreciated that any number of vibrating trays could be used. In addition, it should also be appreciated that the vibrating tray 36b could be positioned at any height in relation to the moving surface 38.

In accordance with a first non-limiting example, the vibrating trays 36a and 36b span the entire length of the moving surface 38. However, in accordance with an alternative embodiment (as shown in FIG. 5b) there are multiple vibrating trays $36b_1$-$36b_5$ that lead towards the moving surface 38. In accordance with a specific example, there is one vibrating tray $36b_1$ for each container 34 that is to be filled. Each of the vibrating trays $36b_1$-$36b_5$ can be controlled independently, such that each of the vibrating trays $36b_1$-$36b_5$ can vibrate at a different frequency, for example. This independent control of the vibrating trays $36b_1$-$36b_5$ enables the container filling machine 10 to have better control over the number of discrete articles for personal treatment that are supplied to each container 34.

In addition, it is possible that instead of vibrating trays 36a and 36b, the transportation device 20 may simply include a hopper, or slanted tray leading towards the moving surface 38. Any device that is operative for feeding the discrete articles for personal treatment towards the moving surface 38 is included within the spirit of the invention.

Figure 5A:
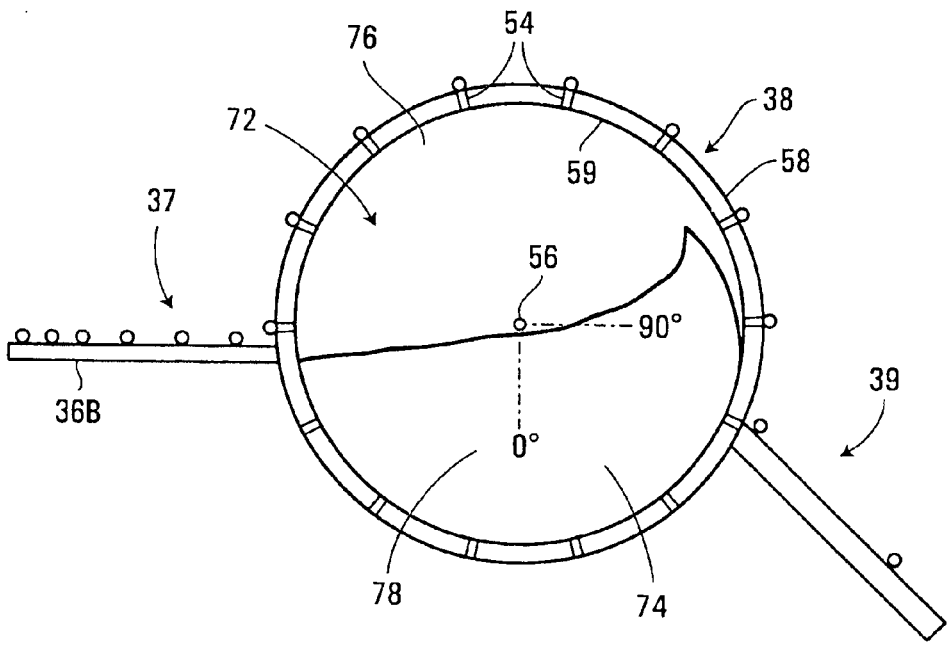
FIG. 5A shows a side representational view of a transportation device in accordance with a non-limiting example of implementation of the present invention.
Figure 5B:
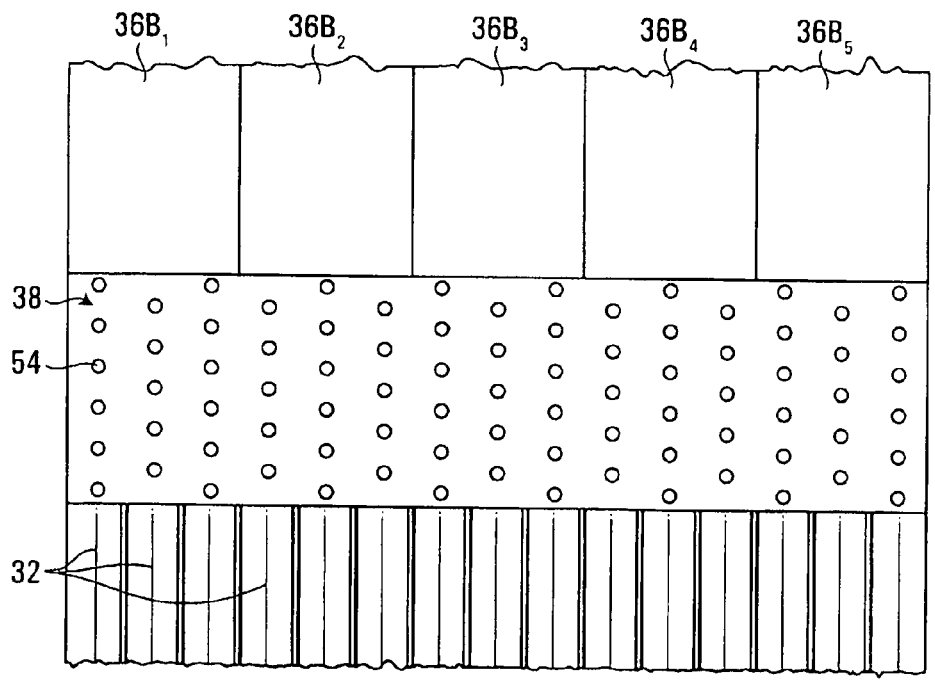
FIG. 5B shows a top representational view of the transportation device of FIG. 5A.

In order to transport the discrete articles for personal treatment from the initial loading position 30 to a drop off position 39, shown in FIG. 5A, the moving surface 38 of the transportation device 20 includes a plurality of spaced-apart air passageways 54 that are arranged in a predetermined pattern thereon. This can best be seen in FIGS. 1 and 5A. The transportation device 20 further includes a vacuum device (not shown) for suctioning air through the plurality of spaced apart air passageways 54. In this manner, the discrete articles for personal treatment that approach the moving surface 38 at a pick-up location 37 are suctioned to the air passageways 54 of the moving surface 38, such that they are distributed over the moving surface 38 in accordance with the predetermined pattern of air passageways 38, and are securely carried by the moving surface 38 in its direction of travel.

As shown in FIG. 5a, the discrete articles for personal treatment are operative to be suctioned to the air passageways 54 of the moving surface 38 at a pick up location 37, and are carried by the moving surface 38 to a drop-off location 39 wherein the discrete articles for personal treatment are no longer carried by the moving surface 38. In other words, the discrete articles for personal treatment are released from being carried by the moving surface 38 at the drop-off location 39.

As mentioned above, the air passageways 54 are arranged on the moving surface 38 in accordance with a predetermined pattern, such that at the drop-off location 39, the discrete articles for personal treatment are spaced from one another in accordance with the predetermined pattern. In one non-limiting example of implementation, the air passageways 54 in the predetermined pattern are evenly spaced from one another, such that the discrete articles for personal treatment are released at the drop-off location 39 in an evenly spaced manner. However, it should be understood that the predetermined pattern may be any pattern possible, such as a random pattern, or an unevenly spaced pattern.

The plurality of air passageways 54 arranged on the moving surface 38 may be of any shape and size. For example, the air passageways 54 may have a cross section that is circular, square, rectangular, octagonal or any other shape, without departing from the spirit of the invention. However, in accordance with a specific non-limiting example of implementation, the air passageways 54 have a cross section that is circular in shape and have a diameter of between 1 mm-10 mm.

The moving surface 38 may be any type of moving surface that is operative for enabling discrete articles for personal treatment to be suctioned thereto and then carried from a pick-up location 37 to a drop-off location 39. For example, the moving surface 38 may be in the form of a conveyer belt, that is either flat or slanted. However, in accordance with the non-limiting embodiment shown in FIGS. 1, 2, 5a and 5b, the moving surface 38 is in the form of a cylindrical drum that is suitable for rotation about a rotation axis 56 in a clock-wise direction.

As best shown in FIGS. 1 and 5b, the plurality of spaced apart air passageways 54 are arranged in rings along the length of the cylindrical drum, and the air passageways 54 in each ring are evenly spaced around a circumference of the cylindrical drum. The cylindrical drum includes an exterior surface 58 and an interior surface 59 that define an interior chamber 72. The plurality of air passageways 54 extend through the drum from the exterior surface 58 to the interior surface 59. In accordance with a non-limiting example, the cylindrical drum has a diameter of between 50 mm-300 mm, however it should be appreciated that a drum having a diameter of any size suitable for its application can be used within the spirit of the invention.

As mentioned above, the vacuum device is operative for suctioning air out of the interior chamber 72 and through the air passageways 54 of the cylindrical drum. In accordance with an alternative non-limiting embodiment, the transportation device 20 may include multiple different vacuum devices (not shown) that are each controlled individually. The individually controlled vacuum devices are operative for suctioning air through the spaced apart air passageways 54 of different regions of the moving surface 38. For example, the cylindrical drum may be divided into 5 distinct regions along its length, (each region corresponding to a container 34 to be filled) wherein each region includes its own vacuum device. In this manner, the container filling machine is better able to control the discrete articles travelling towards each container 34. More specifically, the different vacuum devices can each be controlled separately such that discrete articles for personal treatment that approach the moving surface 38 are suctioned to the moving surface differently along the length of the drum. In this manner, each of the vacuum devices can be controlled independently, which enables the container filling machine 10 to better control the number of discrete articles for personal treatment travelling towards each container 34.

As described above, the number of discrete articles for personal treatment being supplied to each respective container 34 can be controlled via the multiple different vibrating trays $36b_1$-$36b_5$, or via the multiple different vacuum devices (not shown). In general, if multiple vibrating trays $36b_1$-$36b_5$ are used, then only one vacuum device is used. Likewise, if only one vibrating tray 36b is used, then multiple vacuum devices are used. It should however be appreciated that multiple different vacuum devices, and multiple different vibrating trays $36b_1$-$36b_5$ can be used in combination without departing from the spirit of the invention.

The interior chamber 72, or the multiple different interior chambers in the case where the cylindrical drum includes a plurality of vacuum devices, each include a suction blocking device 74 for dividing the interior chamber 72 into a first portion 76 and a second portion 78. The first portion 76 and the second portion 78 are fixed in relation to the rotation of the cylindrical drum, such that the cylindrical drum rotates around the suction blocking device 74. As the air passageways 54 of the cylindrical drum pass by the first portion 76 of the interior chamber 72, air is suctioned through the air passageways 54 by the vacuum device. However, as the air passageways 54 of the cylindrical drum pass by the suction blocking device 74 of the second portion 78, the suction blocking device 74 prevents air from being suctioned through the air passageways 54. Therefore, as the discrete articles for personal treatment that are suctioned to the cylindrical drum pass by the suction blocking device 74, they are released from being carried by the cylindrical drum, and are deposited onto individual paths 32 that run parallel to one another and ultimately lead to a respective container 34. More specifically, it is at the drop-off location 39 that the discrete articles for personal treatment are released onto one of the paths 32 that lead the discrete articles for personal treatment from the drop off location 39 towards a container 34.

As shown in FIG. 5A, the first portion 76 of the interior chamber 72 spans from the pick-up location 37 to the drop-off location 39, such that the discrete articles for personal treatment are suctioned to the air passageways 54 at the pick-up location 37 and are carried by the cylindrical drum to the drop-off location 39. At the drop-off location 39, the suction blocking device 74 prevents the vacuum device from suctioning air through the air passageways 54, such that the discrete articles for personal treatment are released from the air passageways 54 and are deposited onto a respective path 32 that will lead a discrete article for personal treatment into a container. In the non-limiting embodiment shown in FIG. 1, the container filling machine 10 includes 20 paths 32 that eventually feed into 5 containers 34. As such, each set of four paths 32 leads into a respective one of the containers 34. It should be appreciated that the container filling machine 10 may include a different number of paths 32, and may be operative for filling a different number of containers 34, without departing from the spirit of the invention.

The suction blocking device 74 covers a bottom portion of the interior chamber 72, and tapers inwardly from the drop-off location 39 towards the top of the interior chamber 72. In this manner, the suction through the air passageways 54 is strongest from the pick-up location 37 to the top of the interior chamber 72, and then the suction is reduced as the discrete article for personal treatment is carried from the top of the cylindrical drum towards the drop-off location 39. The moving surface relies, in part, on gravity to keep the discrete article for personal treatment in place as the discrete article for personal treatment is carried from the top of the cylindrical drum towards the drop-off location 39. In the embodiment shown in FIG. 5A, the first portion 76 of the interior chamber 72 spans from a first side of the drum to a second side of the drum. As such, the discrete articles for personal treatment are picked up on one side of the drum, carried along a semi-circular path, and then released on the second side of the drum.

In accordance with the non-limiting embodiment shown in FIG. 4, the transportation device 22 is in communication with a processing unit 62 for controlling its operational settings. Such operational settings may include the speed of the moving surface 38, the orientation of the vacuum blocking device 74 (in the case where it is able to move), and/or the level of suction being applied by the vacuum device, among other possibilities.

In a preferred embodiment shown in FIG. 4, the processing unit 62 is part of a computing unit 60 that is operative for controlling the functionality of multiple components of the container filling machine 10. However, in an alternative embodiment, the transportation device 20 may be controlled by a dedicated processing unit that is operative to control only the functionality of the transportation device 20.

The processing unit 62 may be located on the body of the container filling machine 10, or alternatively, the processing unit 62 may be located remotely from the container filling machine 10, such as within a remotely located computer that is in electrical communication with the electrical circuitry of the transportation device 20.

Sensing Device 60

Referring back to FIG. 1, when the discrete articles for personal treatment are released by the transportation device 20 at the drop off location 39, they start travelling along a respective one of the paths 32 towards a container 34. As the discrete articles for personal treatment travel along a respective path 32, they pass through a sensing device 22 that is operative for assessing the integrity of the discrete articles for personal treatment.

As used herein, the term "assessing the integrity of the discrete articles for personal treatment" refers to detecting whether or not a discrete article for personal treatment is defective. An integrally formed discrete article for personal treatment is a non-defective discrete article that is complete and fully formed. As such, by assessing the integrity of the discrete article for personal treatment, the sensing device 22 is verifying whether the discrete article for personal treatment is chipped, broken, or empty in the case of gel cap pills.

Figure 6:
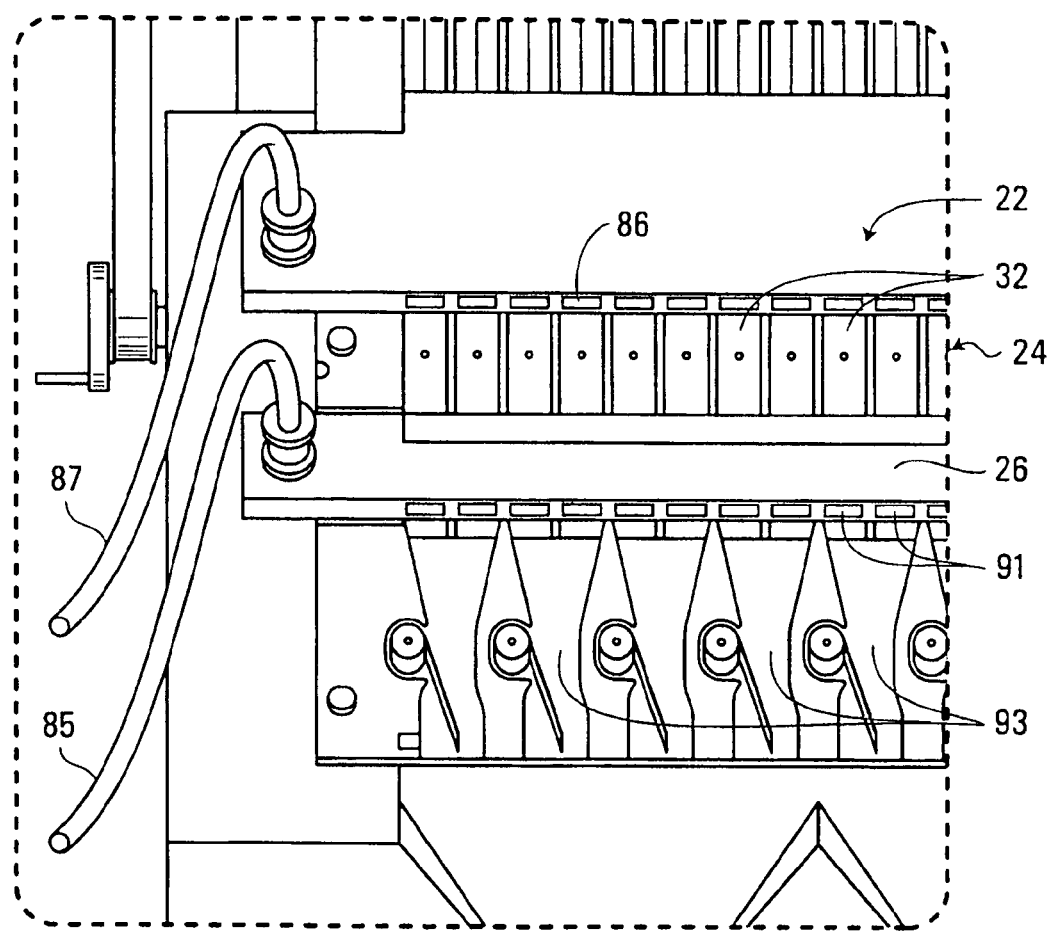
FIG. 6 shows an expanded view of portion 6 shown in FIG. 1.

As shown in FIG. 6, the sensing device 22 includes a plurality of passageways 86, wherein each passageway 86 corresponds to a respective one of the paths 32. Each passageway 86 includes sensing circuitry that operates independently from the sensing circuitry in the other passageways 86. As will be described in more detail below, the sensing circuitry comprises at least one pair of capacitor plates for creating therebetween an electric field. As a discrete article for personal treatment passes through the passageway 86 and between the capacitor plates, the change in capacitance is detected, and is used to determine the integrity of the discrete article for personal treatment.

As shown in FIG. 1, the sensing device 22 is formed of an elongated body 80 of material that can be easily secured to a frame 82 of the container filling machine 10. The elongated body 80 of the sensing device 22 includes sensing circuitry therein, and when secured to the frame 82, defines a plurality of passageways 86 through which the discrete articles for personal treatment can travel. The passageways 86 through the sensing device 22 can be seen in FIG. 6, which shows a blown up portion of FIG. 1. Preferably, the elongated body 80 is constructed out of an FDA approved plastic material that can be easily removed and washed without damaging the sensing circuitry embedded therein. The sensing circuitry is generally embedded within the FDA approved plastic material, such that the circuitry is hermetically enclosed.

Figure 7:
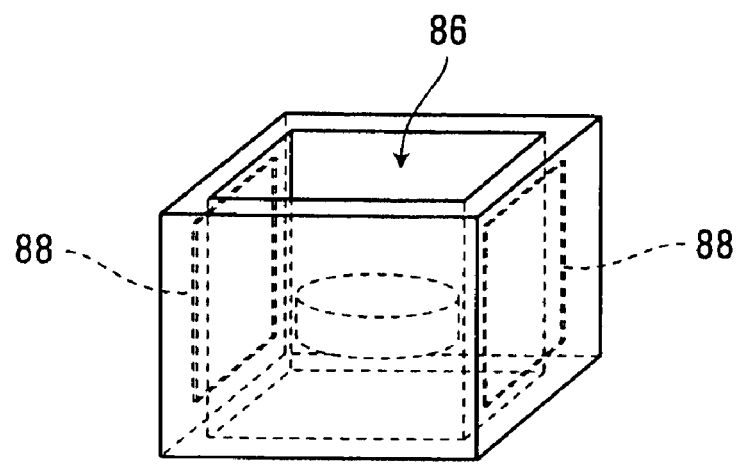
FIG. 7 shows a front perspective view of a portion of a sensing device in accordance with a non-limiting example of implementation of the present invention.

Optionally, the paths 32 of the container filling machine define tracks for guiding the discrete articles for personal treatment through the passageways 86 of the sensing device 22. In the non-limiting embodiment shown in the Figures, each track is in the form of a V-shaped slope that extends through a passageway 86 of the sensing device 22. The slope may range from a 0 degree slope to a 90 degree slope with respect to the reference system shown in FIG. 5A. As a discrete article for personal treatment slides down the slope, the V-shaped side walls prevent non-spherical discrete articles for personal treatment, such as articles having an oblong shape, from tumbling end-over-end, as is often the case when a discrete article for personal treatment simply free-falls through a passageway 86, or just slides down a flat incline. As used herein, the term "tumbling" means to roll end-over-end along one or two different axes in connection with discrete articles for personal treatment that are non-spherical Shown in FIG. 7 is a non-limiting example of a single passageway 86 of the sensing device 22 that is associated with a single path 32. For the sake of simplicity, the functioning of the sensing circuitry will be described with respect to a single passageway 86. It should, however, be appreciated that the circuitry and functionality described with respect to this single passageway 86, can also be found in each of the passageways 86 that form the sensing device 22.

In accordance with the present invention, the sensing circuitry includes a measurement capacitor 88 and a reference capacitor (not shown) associated to each respective passageway 86. The measurement capacitor 88 includes two plates that are positioned on either side of the passageway 86 in a substantially opposing relationship. Specifically, the plates of the measurement capacitor 88 are positioned such that there is one plate located on each side of the passageway 86 for creating therebetween an electric field through which a discrete article for personal treatment will travel. The reference capacitor (not shown) can be realised in many different ways, and in a non-limiting embodiment, may be included within the circuitry contained in the elongated body 80. Alternatively, the reference capacitor may be located elsewhere.

The combination of the measurement capacitor 88 and the reference capacitor (not shown) define a sensing unit. In accordance with a non-limiting embodiment (not shown in FIG. 7), each passageway 86 may include two sensing units, one on top of the other, such that a discrete article for personal treatment travelling through the passageway 86 would be inspected twice, at different points along its path of travel.

Figure 8:
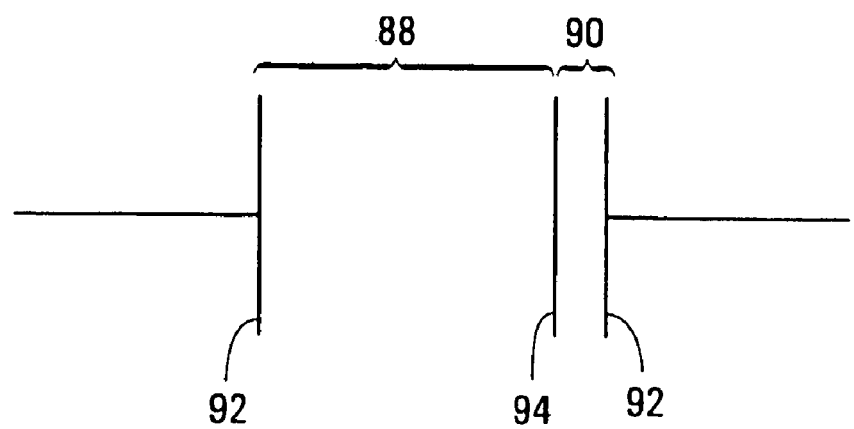
FIG. 8 shows a non-limiting electrical representation of a measurement capacitor and a reference capacitor used in the sensing device of FIG. 7.

Shown in FIG. 8, is an electrical circuit representation of the measurement capacitor 88 and a reference capacitor 90 of a sensing unit. As shown, the measurement capacitor 88 and the reference capacitor 90 each comprise a driven plate 92, meaning a plate to which a voltage is applied from a power source, and a non-driven plate 94, to which no voltage is directly applied. In accordance with the present invention, both the measurement capacitor 88 and the reference capacitor 90 share a common non-driven plate 94.

The purpose of the circuitry contained in each passageway 86 is two-fold. Firstly, the sensing circuitry detects the presence of a discrete article for personal treatment passing therethrough, and secondly the sensing circuitry determines the integrity of the discrete article for personal treatment as the discrete article for personal treatment passes through the passageway 86. The integrity of the discrete article for personal treatment can be determined at least in part on the basis of a change in capacitance manifested by the measurement capacitor 88, as the discrete article for personal treatment passes between the capacitor plates. In short, on the basis of the change in capacitance it can be determined if the mass of the discrete article for personal treatment is correct. An incorrect mass would indicate that the discrete article for personal treatment is defective in some way (i.e. broken, chipped, or not completely filled in the case of a gel-cap).

In accordance with the non-limiting embodiment shown in FIG. 4, the sensing device 22 is in communication with a processing unit 62 that is operative to process the capacitance change detected by the sensing circuitry associated with each passageway. Moreover, the processing unit 62 is operative for processing the capacitance change on the basis of a set of rules and instructions contained in the memory 64, for determining the integrity of a discrete article for personal treatment passing through each respective passageway 86. The processing unit 62 determines, on the basis of the capacitance change detected by the sensing circuitry, whether a discrete article for personal treatment is defective or not. In a preferred embodiment, and as shown in FIG. 4, the processing unit 62 is preferably part of a computing unit 60 that is operative for controlling the functionality of multiple components of the container filling machine 10. However, in an alternative embodiment, the sensing device 22 may be in communication with a processing unit that is dedicated to controlling the functionality of the sensing device 22.

The processing unit may be located within the circuitry in the body 80 of the sensing device 10, or alternatively, the processing unit may be located remotely from the elongated body 80, such as within a remotely located computer that is in electrical communication with one or more components of the container filling machine 10. As shown in FIG. 6, in the case where the processing unit 62 is located remotely from the elongated body 80, the circuitry contained within the elongated body 80 can be electrically connected to the processing unit, via a cable 87.

As mentioned above, as a discrete articles for personal treatment travels through a passageway 86 of the sensing device 22, the discrete article for personal treatment causes a change in capacitance at the measurement capacitor 88 associated to that passageway 86. As this happens, the processing unit 62 is operative for:

1) sensing the change in capacitance as the discrete article for personal treatment passes through the electric field of the measurement capacitor 88; and
2) determining the integrity of the discrete article at least in part on the basis of the change in capacitance in relation to a characteristic signature. The characteristic signature will be described in more detail further on in the specification.

In accordance with a non-limiting example of implementation, once the processing unit 62 has determined the capacitance change at the measurement capacitor 88, it uses program instructions 68 and data 70 stored in the memory 64 to compare that capacitance change to a characteristic signature that corresponds to an integrally formed discrete article for personal treatment. In other words, the characteristic signature corresponds to the capacitance change that would be manifested by the measurement capacitor 88, when a discrete article for personal treatment that is known to be integral, is passed through the measurement capacitor 88. It will be apparent that the characteristic signature will depend on the actual type of discrete article for personal treatment being packaged; as the discrete article changes so will the characteristic signature. For instance, if the discrete article for personal treatment is a medicinal pill, pills of different shapes or weights will be associated with different characteristic signatures. In the case where the capacitance change detected by the processing unit 62 is not within an acceptable range from the characteristic signature, it is determined that the discrete article for personal treatment is defective (i.e. broken, chipped, an empty gel cap or of a shape or kind that does not belong to the batch). In some cases an incorrect discrete article for personal treatment can be accidentally placed into a batch of different discrete articles for personal treatment.

Figure 9:
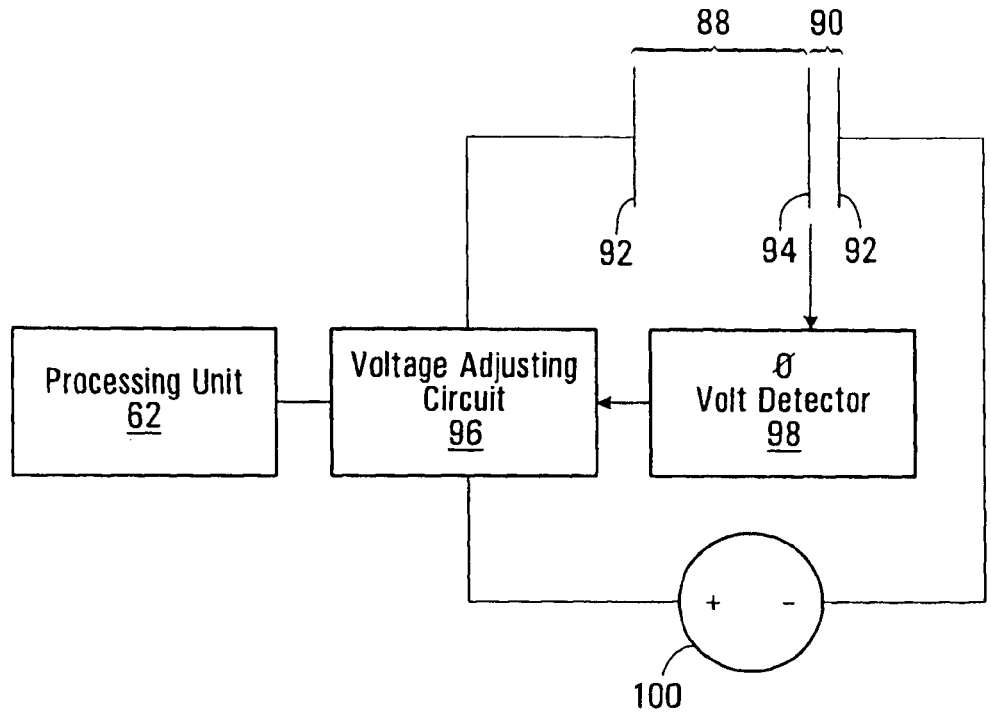
FIG. 9 shows a non-limiting representation of an electrical circuit for the sensing device of FIG. 7.

Shown in FIG. 9 is a non-limiting representation of circuitry used by the sensing device 22 to detect the capacitance change at the measurement capacitor 88. As shown, each measurement capacitor 88 and reference capacitor 90, associated to a passageway 86, includes a voltage adjusting circuit 96, a 0-volt detector 98 and a power supply 100. The power supply 100 is operative for supplying a voltage to the driven plates 92 of the measurement capacitor 88 and the reference capacitor 90. The 0-volt detector 98 is in communication with the non-driven plate 94 of the measurement capacitor 88, and the voltage adjusting circuit 90. The voltage adjusting circuit 96, in turn, is in communication with the power supply 100, the driven plate 92 of the measurement capacitor 88 and the processing unit 62. During the course of operation, the power supply 100 supplies a known voltage to the driven plates 92 of the measurement capacitor 88 and the reference capacitor 90 respectively, such that the non-driven plate 94 is at 0-volts when there is nothing positioned between the two plates of the measurement capacitor 88.

Figure 10:
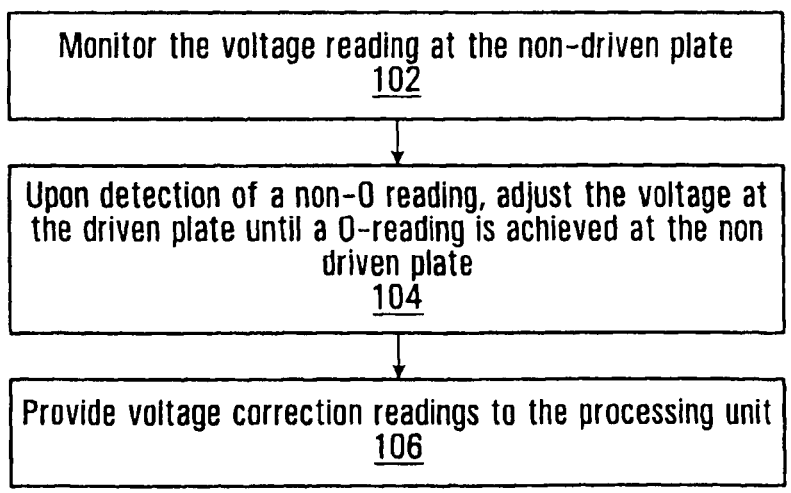
FIG. 10 shows a non-limiting flow diagram of a process used by the sensing device to detect a change in capacitance, in accordance with an example of implementation of the present invention.

The method for determining a capacitance change will now be described in more detail with respect to the flow chart of FIG. 10. As described above, when a discrete article for personal treatment passes through the measurement capacitor 88, the voltage at the non-driven plate 94 changes, as a result of the change of capacitance induced by the discrete article for personal treatment. As shown at step 102, the 0-volt detector 98 is operative for monitoring the voltage at the non-driven plate 94. As a discrete article for personal treatment passes through the measurement capacitor 88, the 0-volt detector 98 detects that the voltage at the non-driven plate 94 has a non-zero reading. The readings taken by the 0-volt detector 98 are then passed to the voltage adjusting circuit 96, such that at step 104, upon detection of a non-0 reading, the voltage adjusting circuit 96 varies the voltage supplied to the driven plate 92 until the non-driven plate 94 goes back to a 0-voltage reading. This detection and correction is done throughout the travel of the discrete article for personal treatment through the measurement capacitor 88. As such it should be appreciated that the voltage correction required may vary over the course of a discrete article for personal treatment's travel through the measurement capacitor 88, such that a graph of voltage adjustment vs. time may provide a type of bell-curve according to certain mathematical functions. At step 106, data describing the voltage correction for the passage of the discrete article for personal treatment are provided to the processing unit 62.

It should be appreciated that the voltage adjusting circuit 96 may provide the values for the voltage correction to the processing unit 62 continuously throughout the voltage correction, such that steps 104, and 106 are performed substantially simultaneously. However, in an alternative embodiment, the voltage adjusting circuit 96 may not provide the values for the voltage correction until the non-driven plate 94 has returned and stabilised to a 0-volt reading, which occurs when the discrete article for personal treatment has left the measurement capacitor 88 At that point the voltage adjusting circuit 96 may then supply the processing unit 62 with all of the voltage correction measurements that occurred during the course of the discrete article's travel through the measurement capacitor 88. Alternatively, the voltage adjusting circuit 96 may supply the processing unit 62 with only a single value, such as the average voltage correction value, or the greatest voltage correction value, among other possibilities.

Once the processing unit 62 has received the data describing the voltage correction value or values, it then determines the change in capacitance at the measurement capacitor 88. More specifically, the level of voltage adjustment indicates the amount of correction required, hence the capacitance change induced by the discrete article for personal treatment. By detecting a capacitance imbalance between the measurement capacitor 88 and the reference capacitor 90, the processing unit 62 detects a difference in the change of capacitance between the two capacitors. In a preferred embodiment, reference capacitor 90 maintains a constant capacitance throughout the course of operation. As such, by detecting the capacitance change at the measurement capacitor 88, the processing unit 62 is also detecting a difference in capacitance change between the measurement capacitor 88 and the reference capacitor 90.

Once the change in capacitance at the measurement capacitor 88 has been detected, the processing unit 62 determines the integrity of the discrete article for personal treatment at least in part on the basis of the change in capacitance and a characteristic capacitance change signature. The processing unit 62 will analyse, over time, the voltage correction necessary to balance the capacitors, so as to determine a change in capacitance. The processing unit 62 then compares the change in capacitance at the measurement capacitor 88 with a characteristic capacitance change signature. As mentioned above, the change in capacitance at the measurement capacitor 88 may be a single value, such as the maximum amount of voltage that was applied by the voltage adjusting circuit 96 during the course of the voltage correction, or the change in capacitance may be expressed as a set of values versus time, thus describing a curve or pattern.

In accordance with a preferred embodiment, the characteristic capacitance change signature may be stored in the memory 64 of the computing unit 100, such that the processing unit 62 can access it when needed. The characteristic capacitance change signature stored in the memory may be expressed in different ways depending on the intended application. For instance the characteristic capacitance change signature may be the maximal voltage value applied by the voltage adjusting circuit 96, or as a set of values describing the voltage correction variation over time. Multiple characteristic capacitance change signatures that are associated to different discrete articles for personal treatment may be stored in the memory. For example, in the case where the container filling machine 10 is operative for processing a plurality of different kinds of discrete articles for personal treatment, there may be a separate characteristic capacitance change signature for each of the different kinds of discrete articles for personal treatment.

The characteristic capacitance change signature may be entered into the memory 64 in a variety of different ways. In accordance with a first non-limiting example, the values may be pre-stored in the memory 64 of the computing unit by a manufacturer of the container filling machine 10, or by a software provider. Alternatively, the characteristic capacitance change signature may be entered by a user into the memory 64 via the user inputs 52. This could be done each time a new type of discrete article for personal treatment is being loaded into one or more containers.

In accordance with an alternative embodiment, the characteristic capacitance change signature value or values may be derived by the sensing device 22 at least in part on the basis of capacitance change values that occur when a plurality of known integral discrete articles for personal treatment are passed through the measurement capacitor 88. More specifically, by passing a few known integral discrete articles for personal treatment through the measurement capacitor, and determining the corresponding capacitance change caused by these integral discrete articles for personal treatment, the characteristic capacitance change signature can be derived. In this manner, the sensing device 22 is able to self calibrate.

In the case where the container filling machine 10 is operative for self-calibrating, an operator of the machine 10 would enter a few known integral discrete articles for personal treatment through the machine. The processing unit 62 would then receive the voltage correction values for these known integral discrete articles for personal treatment from the voltage adjusting circuit 96. Based on these values, or the voltage versus time curves formed by these values, the processing unit 62 establishes a value, or a set of values versus time, that define a characteristic capacitance change signature for an integral discrete article for personal treatment. As such, if the voltage correction value or values for an unknown discrete article for personal treatment match those of the characteristic capacitance change signature, then it can be determined that the unknown discrete article for personal treatment is an integral discrete article for personal treatment. Whereas, if the voltage correction values do not fall within the characteristic capacitance change signature, then the discrete article for personal treatment is determined to be defective.

The comparison logic used to determine if the capacitance change observed at the measurement capacitor 88 matches a given characteristic capacitance change signature may widely vary without departing from the spirit of the invention. When the characteristic capacitance change signature is expressed as a single maximal voltage adjustment value and the capacitance change at the measurement capacitor 88 is also expressed as a single maximal adjustment value, the two values are compared and if they match within a certain tolerance, the comparison logic concludes that the discrete article for personal treatment is integral. In the instance where the characteristic capacitance change signature and the capacitance change at the measurement capacitor 88 are expressed as voltage variations over time, where the time is the interval required for the discrete article for personal treatment to pass through the measurement capacitor 88, the comparison may require different techniques to establish the extent to which the measurement curve matches the signature curve. The comparison may include comparing first the maximal voltage values and then comparing another parameter which takes into account the time factor. For example, the other parameter can be the surface area under the curve established by computing the integral of the curve, among other possibilities.

The reader skilled in the art will appreciate that many other comparison techniques can be used to determine if the capacitance change at the measurement capacitor 88 matches the characteristic capacitance change signature and that the present invention is not limited to any particular one of those techniques.

It should be appreciated that the processing unit 62 is operative for simultaneously receiving and processing signals from each of the voltage adjusting circuits 96 associated with each one of the respective passageways 86 of the sensing device 22. As such, in the case of the container filling machine 10 shown in FIG. 1, the processing unit 62 is operative to receive signals from twenty separate voltage adjusting circuits 96 at approximately the same time. In such a case, the voltage adjusting circuits 96 are operative for providing identification information to the processing unit 62, along with their voltage adjustment readings, such that in the case where a defective discrete article for personal treatment is identified, the processing unit 62 is able to determine along which path 32 the defective discrete article for personal treatment was detected.

In accordance with the present invention, the measurement capacitor 88 and the reference capacitor 90 are operative to function at a relatively low voltage. Preferably, the power supply 100 is operative to supply less than 120V to the capacitors 88, 90. More preferably, the power supply 100 is operative to supply less than 100 V to the capacitors 88, 90. Still more preferably, the power supply 100 is operative to supply less than 50V to the capacitors 88, 90. And still more preferably, the power supply 100 is operative to supply less than 20V to the capacitors 88, 90. Advantageously, the sensing circuitry that includes the 0-volt detector 98 and the voltage adjusting circuit 96 allows the detection of a capacitance change while operating at a relatively low voltage in comparison to existing capacitance sensing arrangements. Operating at a low voltage results in a safer, more efficient system. The low voltage further helps to reduce electrostatic dust build-up and wear on the sensing device 22.

In the case where the processing unit 62 determines that a discrete article for personal treatment that has passed through the sensing device 22 is defective, the processing unit 62 issues a signal to the rejection device 24, such that the defective discrete article for personal treatment can be removed from continuing along its path 32 towards a container. The rejection device 24 will now be described in more detail below.

Rejection Device 24

Associated to each one of the paths 32 is a rejection device 24. As shown in FIGS. 1 and 2, each rejection device 24 is positioned along a respective path 32 after the sensing device 22. More specifically, each rejection device 24 is positioned between the sensing device 22 and the counting device 26 (which will be described in more detail below). For the sake of simplicity, only one rejection device 24 will be described in more detail below. However, it should be appreciated that the below description applies to all of the rejection devices 24 contained in the container filling machine 10.

As described above, in the case where the sensing device 22 detects that a defective discrete article for personal treatment is travelling along one of the paths 32, the rejection device 24 associated to that path 32 is operative to remove the defective discrete article for personal treatment from continued travel along its path 32 towards a container 34.

Figure 11:
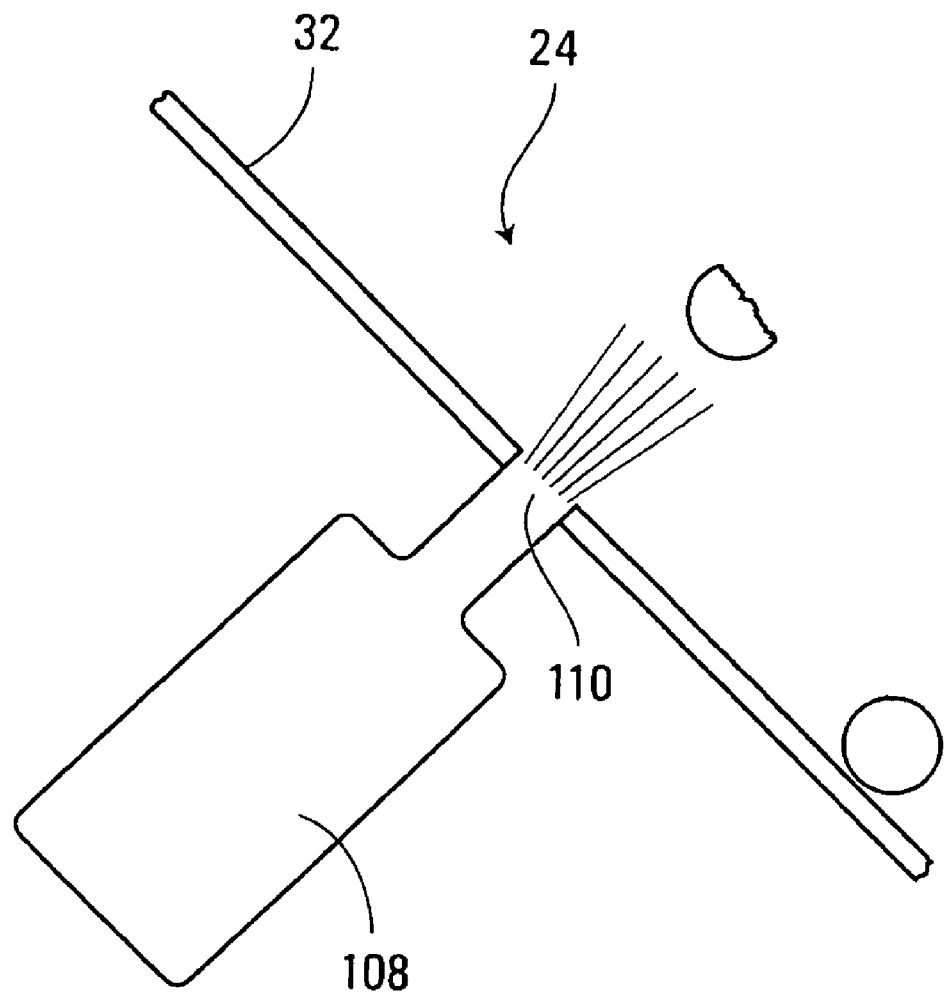
FIG. 11 shows a side representational view of a rejection device in accordance with a non-limiting example of implementation of the present invention.

Shown in FIG. 11 is a non-limiting example of a rejection device 24 in accordance with the present invention. In the embodiment shown, the rejection device 24 includes a canister of compressed air 108 positioned behind the path 32. The opening of the canister 108 is aligned with an aperture 110 in the path 32. As such, when not in use, the rejection device 24 does not interfere with the travel of a non-defective discrete article for personal treatment along the path 32. It should be appreciated that each rejection device 24 may include a separate canister of compressed air, as shown in FIG. 11, or alternatively, each rejection device 24 may be connected to a common canister of compressed air. In such a case, the supply of compressed air to each one of the apertures 110 would be controlled via a separate valve leading to each one of the apertures 110 in the container filling machine 10. Any suitable manner known in the art for mounting the one or more canisters of compressed air to the frame of the container filling device can be used without departing from the spirit of the invention.

In accordance with the non-limiting embodiment shown in FIG. 4, each rejection device 24 is in communication with a processing unit 62, that is operative to activate the rejection device 24 in the case where a defective discrete article for personal treatment has been detected. Each rejection device 24 may be in communication with a common processing unit 62, or with a separate processing unit. In a preferred embodiment, and as shown in FIG. 4, each rejection device 24 is in communication with a common processing unit 62, that is preferably part of a computing unit 60 that is operative for controlling the functionality of multiple components of the container filling machine 10. In an alternative embodiment, the plurality of rejection devices 24, or each individual rejection device 24, may be in communication with a processing unit that is dedicated to controlling only the functionality of, the one or more rejection devices 24.

In operation, the processing unit 62 that controls each rejection device 24 is operative to receive a signal indicating that the sensing device 22 has identified a defective discrete article for personal treatment travelling along one of the paths 32. Upon receipt of such a signal, the processing unit 62 causes the rejection device 24 associated to that path 32 to remove the discrete article for personal treatment from continued travel along that path 32. In the case where the rejection device 24 includes a canister of compressed air, the processing unit 62 causes the rejection device 24 to release a jet of compressed air as the defective discrete article for personal treatment passes in front of the aperture 110 corresponding to that path 32. In this manner, the discrete article for personal treatment is blown off the path 32 and removed from continued travel towards a container.

The release of the jet of compressed air may be timed by the processing unit 62 such that the air is released exactly as the discrete article for personal treatment passes by the aperture 110 in the path 32. Alternatively, the release of compressed air may commence immediately upon detection at the sensing device 22 of a defective discrete article for personal treatment, such that when the discrete article for personal treatment reaches the stream of air, it hits the stream of air and is blown off its path of travel.

In the case where the rejection device 24 is in communication with a processing unit 62 that also controls the functionality of the sensing device 22, the processing unit 62 will be aware when the sensing unit 22 has detected a defective discrete article for personal treatment, and can then cause the activation of the rejection device 24. However, in the case where the rejection devices 24 are controlled by a dedicated processing unit, that processing unit is in communication with the processing unit of the sensing device 22, such that it can receive a signal indicative that a defective discrete article for personal treatment has been detected, and thus activate the appropriate rejection device 24.

In the case where each rejection device 24 is controlled by a common processing unit 62, the processing unit 62 is operative to control each of the rejection devices at the same time such that they can each operate independently of each other.

Although not shown in the Figures, a collection vessel, such as a bucket, can be positioned just beyond the paths 32, such that any defective discrete articles for personal treatment that are ejected from their paths 32 by the rejection device 24 are collected in the vessel. Such a vessel can be emptied periodically in order to discard the defective discrete articles for personal treatment.

Although the rejection device 24 shown in FIG. 11 uses a jet of compressed air in order to remove a defective discrete article for personal treatment from its path of travel, it should be appreciated that any suitable device for removing a defective discrete article for personal treatment could be used. For example, the rejection device 24 could be a mechanical device, such as a spring-loaded rod, or trap door that opens when a defective discrete article for personal treatment passes by. Alternatively, the rejection device may still use compressed air, but in an indirect manner. For example, the jet of compressed air may cause a plate that is lying along the path 32 to swing outwards thus pushing a discrete article for personal treatment passing across the plate to be ejected from the path 32. It should be appreciated that any device that is operative for removing a defective discrete article for personal treatment from continued travel along a path 32 towards a container is included within the scope of the present application.

Counting Device 26

Referring back to FIG. 1, located after each rejection device 24 is a counting device 26 for counting the integral discrete articles for personal treatment that successfully pass by the rejection device 24. The purpose of the counting device 26 is to obtain a count of the integral discrete articles for personal treatment in order to ensure that a proper number of discrete articles for personal treatment are placed in each container 34.

In the non-limiting embodiment shown, the counting device 26 is formed of an elongated body 112 of material that can be easily secured to the frame 82 of the container filling machine 10. When connected to the frame, the elongated body 112 defines a plurality of passageways 91 through which the discrete articles for personal treatment can travel. Each passageway 91 is associated to a respective one of the paths 32 and includes circuitry for detecting when a discrete article for personal treatment passes therethrough. More specifically, each one of the passageways 91 includes circuitry that functions independently of each other passageway 91. Preferably, this elongated body 112 is constructed out of a plastic material that can be easily removed and washed without damaging the circuitry embedded therein.

In accordance with the non-limiting embodiment shown in FIG. 4, the counting device 26 is in communication with a processing unit 62, that is operative to detect and count the discrete articles for personal treatment passing through each passageway 91 of the counting device 26. The processing unit 62 is in communication with the circuitry of each passageway 91 for detecting when a discrete article for personal treatment passes through each passageway 91, and for keeping a count of the number of discrete articles for personal treatment that pass through each passageway 91. In accordance with a non-limiting embodiment, the processing unit 62 may include a counter associated to each passageway, such that each counter increments each time a discrete article for personal treatment passes through its respective passageway.

In a preferred embodiment, and as shown in FIG. 4, the counting device 26 is in communication with a processing unit 62 that is part of a computing unit 60 that controls the functionality of multiple components of the container filling machine 10. However, in an alternative embodiment, the counting device 26 may be in communication with a processing unit that is dedicated to controlling the functionality of the counting device 26. The processing unit may be located within the circuitry in the elongated body 112, or alternatively, the processing unit may be located remotely from the elongated body 112, such as within a remotely located computer. As shown in FIG. 6, in the case where the processing unit 62 is located remotely from the elongated body 112, the counting circuitry contained within the elongated body 112 is electrically connected to the processing unit 62, via a cable 85.

Preferably, the processing unit 62 is operative for simultaneously receiving and processing signals from the counting circuitry associated with each one of the passageways 91 of the counting device 26. As such, in the case of the container filling machine 10 shown in FIG. 1, the processing unit 62 is operative to receive signals from twenty separate passageways at approximately the same time. In such a case, the circuitry associated to each passageway 91 is operative for providing identification information to the processing unit 62, such that the processing unit 62 is able to keep an appropriate count of the discrete articles for personal treatment passing through each respective passageway 91.

The circuitry contained within each passageway 91 may be any suitable circuitry for detecting when a discrete article for personal treatment passes through the passageway 91. For example, the counting device 26 may include optical circuitry or capacitance circuitry without departing from the spirit of the invention. Once the circuitry detects that an object, such as a discrete article for personal treatment, has passed through the passageway 91, a signal is sent to the processing unit 62, such that the processing unit 62 can keep a count of the number of discrete articles for personal treatment that have passed through each passageway 91.

The purpose of the counting device 26 is to help control the number of discrete articles for personal treatment entering each container 34.

Path Blocking Devices 28

Figure 12:
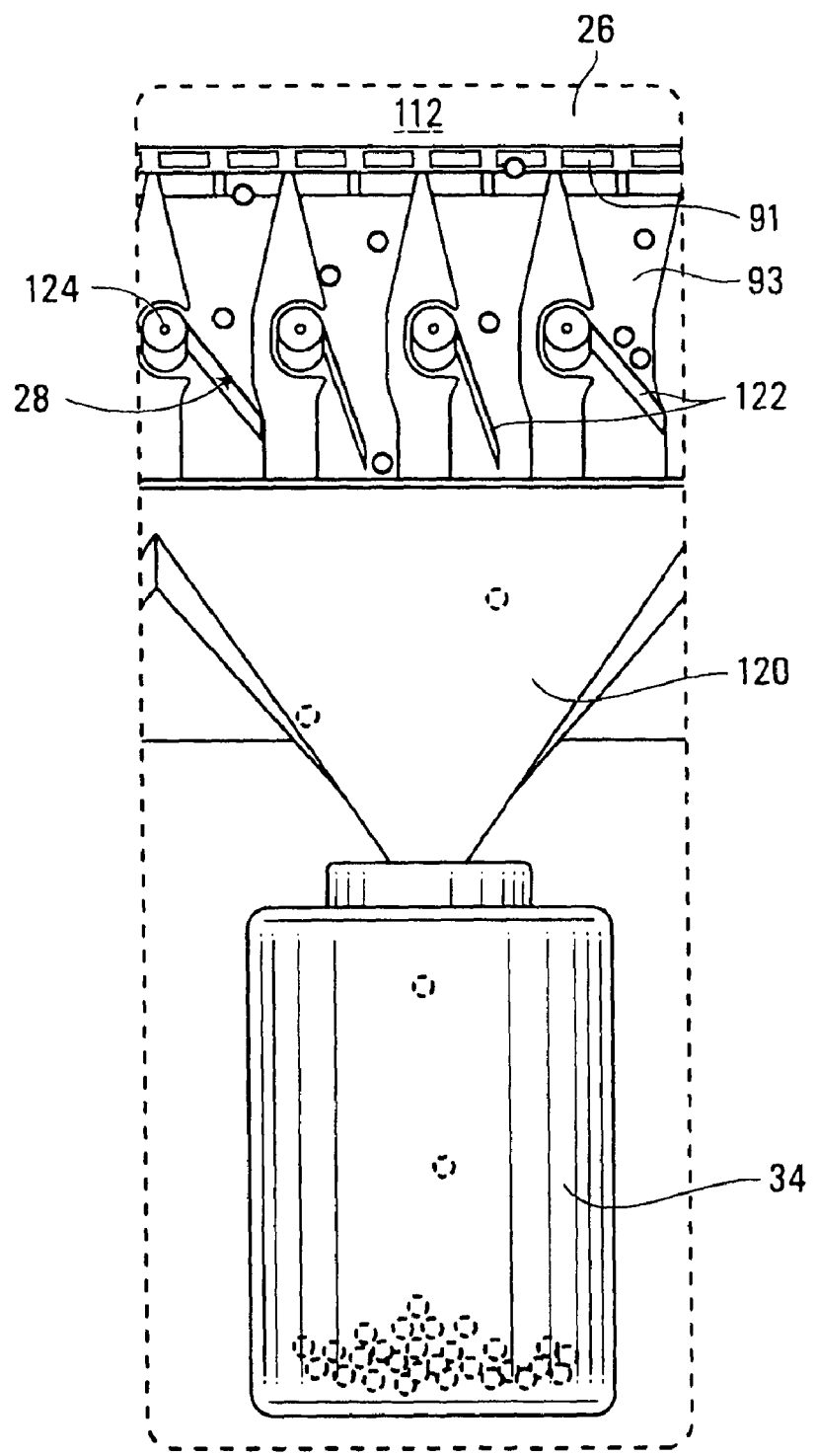
FIG. 12 shows an expanded view of portion 12 shown in FIG. 1.

In the non-limiting embodiment shown in FIG. 1, multiple paths 32 lead to a single container 34. More specifically, and as best shown in FIG. 12, eight paths 32 lead into four expanded paths 93, which in turn lead into a funnel that directs the discrete articles into a respective container 34. It should, however, be appreciated that any number of paths 32 could lead into any number of containers 34, without departing from the spirit of the invention. For example, there may be a one-to-one ratio, with each path 32 leading into a separate respective container.

As shown in FIGS. 6 and 12, positioned between the counting device 26 and a container 34 are a plurality of path blocking devices 28; namely one path blocking device 28 for each one of the expanded paths 93. Each one of the expanded paths 93 feeds into a funnel 120 which, in turn, leads into a container 34. Although in the Figures, each one of the paths 32 leads into an expanded path 93, which in turn has a respective path blocking device 28, it should be appreciated that in an alternative embodiment, there may be one path blocking device 28 for each one of the paths 32 and thus for each one of the counting devices 26. As such, the paths 32 do not combine into expanded paths 93 until after the path blocking devices 28.

In combination with the counting device 26, the path blocking devices 28 are operative for controlling the number of discrete articles for personal treatment that enter each container. More specifically, the path blocking devices 28 are operative to move between an open position and a closed position in order to block the travel of the discrete articles for personal treatment into a container. As shown in FIG. 12, the right-most path blocking device 28 is in a closed position, wherein the discrete articles for personal treatment travelling along that expanded path 93 are prevented from travelling into the container 34. Whereas, the two middle path blocking devices 28 are in an open position, such that the discrete articles for personal treatment travelling along those paths are able to travel past the path blocking devices 28 into the container 34.

As shown in FIG. 4, the path blocking devices 28 are in communication with the processing unit 62, such that the processing unit 62 can control the movement of the path blocking devices 28 between the open position and the closed position. In a preferred embodiment, and as shown in FIG. 4, the path blocking devices 28 are in communication with a processing unit 62 that is also in communication with the counting device 26, as well as the other components in the container filling machine. It should be appreciated however that a processing unit 62 dedicated to the control of the path blocking devices 28 could also be used without departing from the spirit of the invention. In such a case, the processing unit would be operative for receiving information from the counting device 26 indicative of a count of the number of discrete articles for personal treatment passing through respective passageways.

In operation, the processing unit 62 controls the movement of the path blocking devices 28 at least in part on the basis of information received from the counting device 26 and the number of discrete articles for personal treatment that should be supplied to each container. The information received from the counting device 26 is generally indicative of the number of discrete articles for personal treatment that have passed through each passageway 91 of the counting device 26. The processing unit 62 processes this information in accordance with program instructions 68 stored in the memory 64. Such program instructions may include a specific algorithm, such that the control of the path blocking devices 28 is performed in accordance with a predefined algorithm. Any algorithm suitable for controlling the number of discrete articles for personal treatment that enter each container 34 is included within the scope of the present invention. For example, in the case where each container 34 is to be filled with one hundred discrete articles for personal treatment, and there are four expanded paths 93 leading into each container, the algorithm may specify that each path blocking device closes after twenty five discrete articles for personal treatment have passed by each path blocking device 28. Alternatively, three of the path blocking devices 28 may close after 24 discrete articles for personal treatment have passed by, and the fourth gate may close after 28 discrete articles for personal treatment have passed by. In this way, the fourth path blocking device 28 is able to more precisely monitor the final discrete articles for personal treatment entering the container 34. It should be appreciated that a variety of different algorithms can be used in order to control the functioning of the path blocking devices 28, without departing from the spirit of the invention.

In the non-limiting embodiment shown in FIGS. 1, 2 and 12, the path blocking devices 28 are in the form of gateways 122 that pivot about a pin 124 mounted to one side of the path 32. The gateways 122 pivot about the pin 124 in order to move between the open position and the closed position. In the closed position, the gateway 122 forms a physical barrier that spans across the width of a path 93. Whereas in the open position, the gateway 122 is positioned along the length of the path 93 such that discrete articles for personal treatment can pass by the gateway 122 and enter a container 34.

Although the path blocking devices 28 shown in the Figures include a gateway 122 for blocking their respective paths 93, it should be appreciated that any suitable device for blocking a path 93 or 32 could be used. For example, the path blocking device 28 could be a different type of barrier that is embedded within the path, and springs up when needed. Alternatively, the path blocking device may be a suction device that temporarily restrains the discrete articles for personal treatment via a vacuum suction. Any device that is operative for temporarily blocking the discrete articles for personal treatment from continued travel towards a container 34 is included within the scope of the present application.

The path blocking devices 28 are further operative for preventing discrete articles for personal treatment from continued travel while the filled containers 34 are being replaced by new containers 34. More specifically, when the containers 34 have been filled with the appropriate number of discrete articles for personal treatment, all of the path blocking devices 28 close. As such, the filled containers 34 can be removed and replaced with new containers without stopping the flow of discrete articles for personal treatment through the sensing device 22, the rejection device 24 and the counting device 26. Instead, the discrete articles for personal treatment simply accumulate at the path blocking devices 28. When the new containers 34 are in place underneath the funnels 120, the path blocking devices 28 open, and the discrete articles for personal treatment that have accumulated enter the new containers. In this manner, the flow of discrete articles for personal treatment through the container filling machine 10 does not slow down or stop for a container change.

Multiple Machines

Figure 13A:
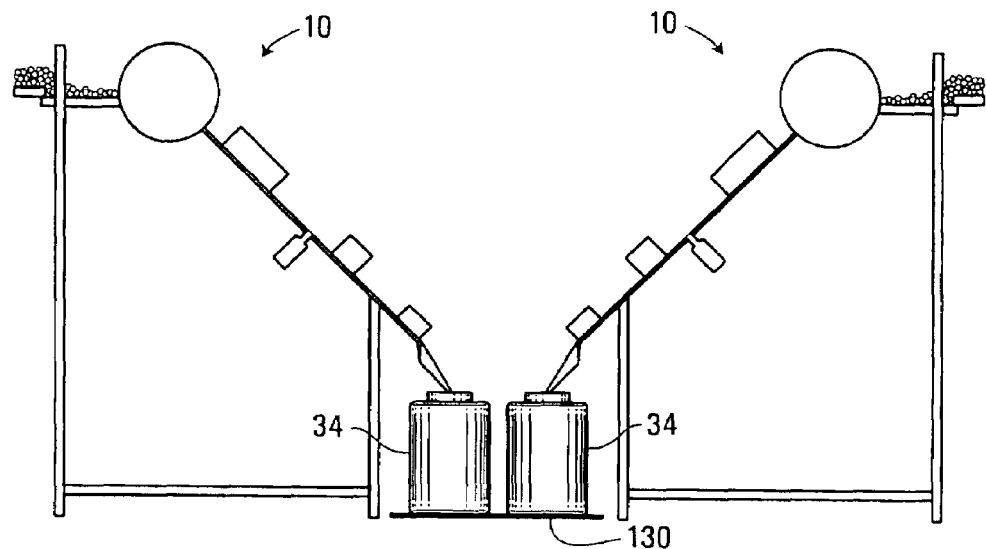
FIG. 13A shows a first non-limiting configuration for using two of the container filling machines of FIG. 1 simultaneously.
Figure 13B:
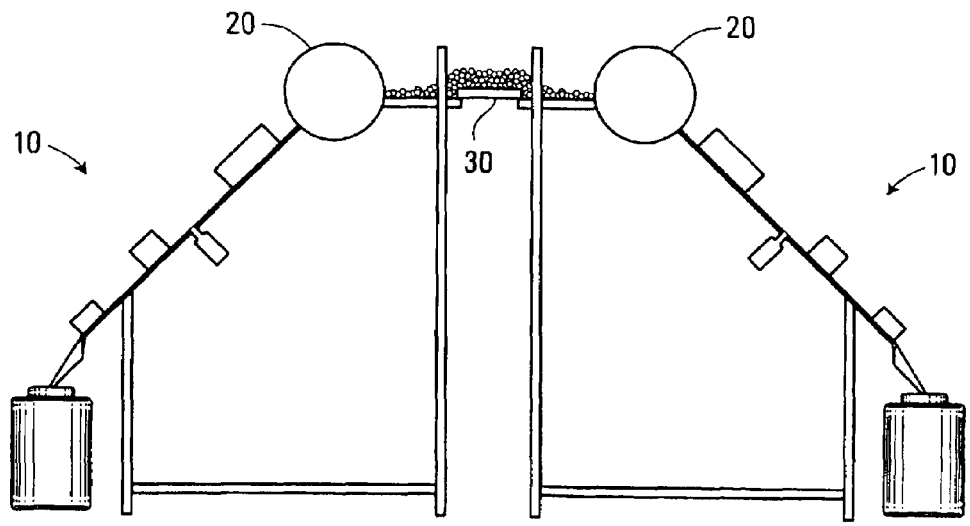
FIG. 13B shows a second non-limiting configuration for using two of the container filling machines of FIG. 1 simultaneously.

As shown in FIGS. 13A and 13B, two or more container filling machines 10, as described above, can be used in combination in order to fill more containers simultaneously.

Shown in FIG. 13A are two container filling machines 10 positioned facing each other, such that two rows of containers 34 may be positioned on a single conveyor belt 130. The conveyor belt 130 is operative for transporting empty containers towards the container filling machines 10, and filled containers away from the container filling machines 10 towards a capping station, for example.

Shown in FIG. 13B are two container filling machines 10 positioned back-to-back, such that they may share the same initial loading location 30. As such, an initial supply of discrete articles for personal treatment can be loaded into the common loading location 30 and then travel towards one of the two transportation devices 20.

Figure 13C:
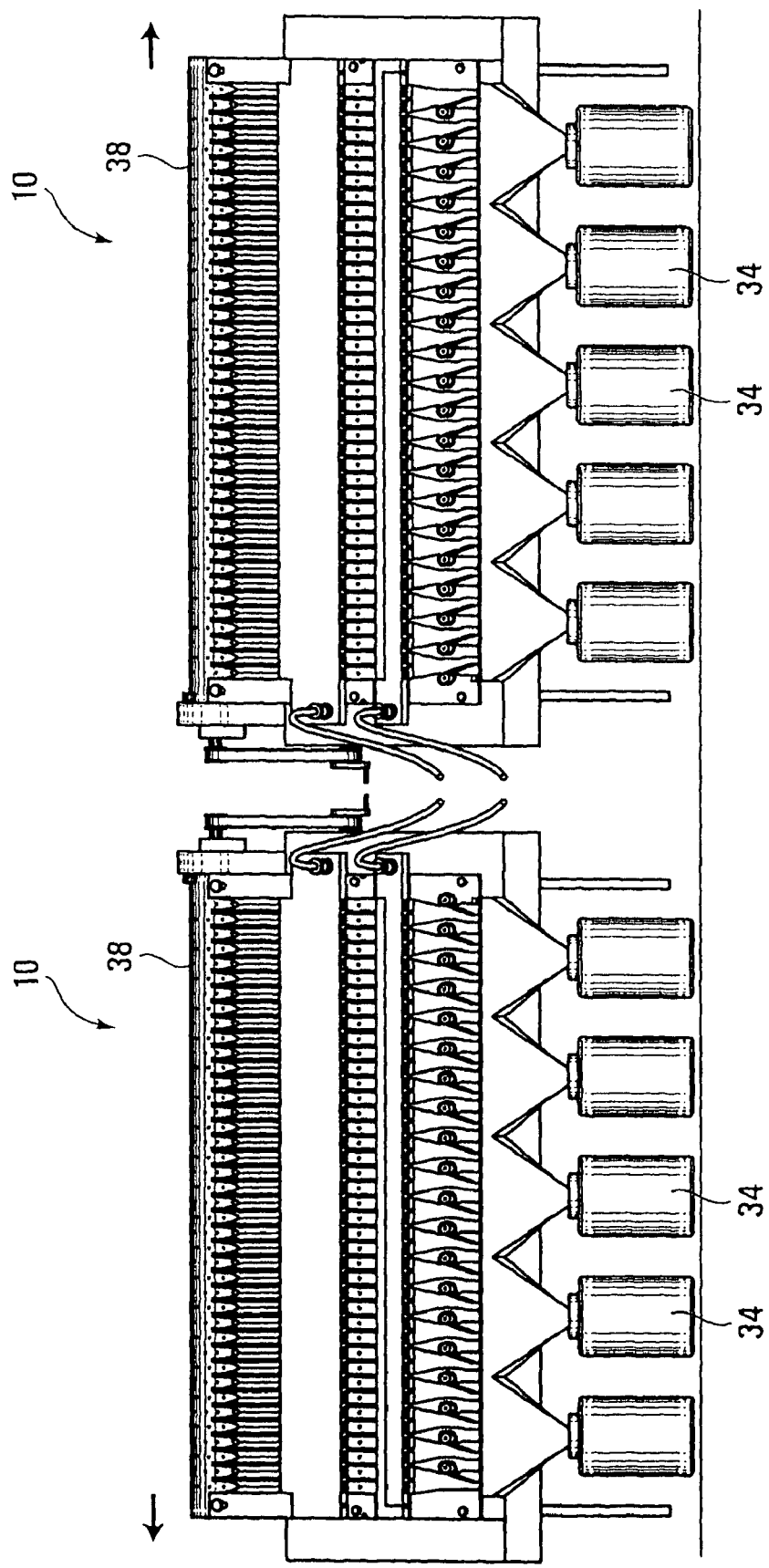
FIG. 13C shows a third non-limiting configuration for using two of the container filling machines of FIG. 1 simultaneously.

Shown in FIG. 13C are two container filling machines 10 positioned side-by-side such that they may share the same initial loading location, and the same conveyor belt for transporting the containers 34. Each of the cylindrical drums that form the moving surfaces 38 can be accessed from opposite ends of the two-machine set up.

It should be appreciated that one or more container filling machines 10 can be used in combination, and can be placed in any configuration with respect to each other, without departing from the spirit of the invention.

Although the present invention has been described in considerable detail with reference to certain preferred embodiments thereof, variations and refinements are possible without departing from the spirit of the invention. Therefore, the scope of the invention should be limited only by the appended claims and their equivalents.

The invention claimed is:

1. A sensing device suitable for use with a container filling machine, said sensing device being operative for detecting the integrity of discrete articles for personal treatment to be loaded in a container, said sensing device comprising:
   a) a measurement capacitor;
   b) a reference capacitor; and
   c) a processing unit in communication with said measurement capacitor and said reference capacitor, said processing unit being operative for:
      i) detecting a difference in capacitance change between said measurement capacitor and said reference capacitor as a discrete article for personal treatment passes through said measurement capacitor;
      ii) determining the integrity of the discrete article for personal treatment at least in part on the basis of said difference in capacitance change; and
      iii) upon a determination that the discrete article for personal treatment is defective, causing the discrete article for personal treatment to be removed from continued travel towards the container.

2. A sensing device as defined in claim 1, wherein said processing unit determines the integrity of the discrete article for personal treatment at least in part on the basis of said difference in capacitance change and a characteristic capacitance change signature.

3. A sensing device as defined in claim 2, wherein said processing unit determines the integrity of the discrete article for personal treatment by comparing said difference in capacitance change with said characteristic capacitance change signature.

4. A sensing device as defined in claim 2, wherein said processing unit is operative for deriving said characteristic capacitance change signature at least in part on the basis of capacitance change values that are generated when a plurality of integral discrete articles for personal treatment are passed through said measurement capacitor.

5. A sensing device as defined in claim 3, wherein comparing said difference in capacitance change with said characteristic capacitance change signature involves determining whether said difference in capacitance change matches said characteristic capacitance change signature within a predetermined tolerance.

6. A sensing device as defined in claim 1, wherein said measurement capacitor and said reference capacitor each comprise a driven plate and a non-driven plate.

7. A sensing device as defined in claim 6, wherein said measurement capacitor and said reference capacitor share a common non-driven plate.

8. A sensing device as defined in claim 1, further comprising a voltage adjusting circuit for adjusting a voltage supplied to said driven plate of said measurement capacitor in response to a change in voltage at said non-driven plate when a discrete article for personal treatment passes through said measurement capacitor.

9. A sensing device as defined in claim 8, wherein said voltage adjusting circuit adjusts the voltage supplied to said driven plate of said measurement capacitor until the voltage at said non-driven plate reaches a predetermined reference voltage.

10. A sensing device as defined in claim 9, wherein said processing unit determines the difference in capacitance change at least in part on the basis of the voltage adjustment controlled by said voltage adjusting circuit for causing the non-driven plate to reach the predetermined reference voltage.

11. A sensing device as defined in claim 1, further comprising a track for guiding discrete articles for personal treatment through said measurement capacitor, said track being operative for preventing the discrete articles for personal treatment from tumbling as they pass through said measurement capacitor.

12. A sensing device as defined in claim 11, wherein said track includes a V-shaped slope.

13. A sensing device as defined in claim 1, wherein said measurement capacitor and said reference capacitor have a voltage of less than 50V.

14. A sensing device as defined in claim 1, wherein said measurement capacitor and said reference capacitor have a voltage of less than 20V.

15. A sensing device as defined in claim 1, wherein said measurement capacitor and said reference capacitor have a voltage of less than 10V.

16. A sensing device as defined in claim 1, wherein said discrete articles for personal treatment are one of gel caps and powder pills.

17. A sensing device as defined in claim 1, wherein said discrete articles for personal treatment are cosmetic items.

18. A sensing device as defined in claim 1, wherein causing the discrete article for personal treatment to be removed from continued travel towards the container comprises generating a signal indicative of a defective discrete article for personal treatment.

19. A sensing device as defined in claim 18, further comprising issuing the signal indicative of the defective discrete article to a rejection device for causing the discrete article for personal treatment to be removed from travelling along a path towards the container.

20. A method for detecting the integrity of discrete articles for personal treatment to be loaded in a container, said method comprising:
  a) providing a measurement capacitor;
  b) providing a reference capacitor;
  c) detecting a difference in capacitance change between the measurement capacitor and the reference capacitor when a discrete article for personal treatment passes through the measurement capacitor;
  d) determining the integrity of the discrete article for personal treatment at least in part on the basis of the difference in capacitance change
  e) upon determining that the discrete article for personal treatment is defective, causing the discrete article for personal treatment to be removed from continued travel towards the container.

21. A method as defined in claim 20, wherein the integrity of the discrete article for personal treatment is determined at least in part on the basis of a characteristic capacitance change signature.

22. A method as defined in claim 21, wherein determining the integrity of the discrete article for personal treatment involves comparing the difference in capacitance change with the characteristic capacitance change signature.

23. A method as defined in claim 22, wherein the measurement capacitor and the reference capacitor each comprise a driven plate and share a common non-driven plate, said method further comprising adjusting a voltage supplied to the driven plate of the measurement capacitor in response to a change in voltage at the non-driven plate when a discrete article for personal treatment passes through the measurement capacitor.

24. A method as defined in claim 23, wherein the voltage supplied to the driven plate of the measurement capacitor is adjusted until the voltage at said non-driven plate reaches a predetermined reference voltage.

25. A method as defined in claim 24, wherein the difference in capacitance change is determined at least in part on the basis of the voltage adjustment for causing the non-driven plate to reach the predetermined reference voltage.

26. A sensing device suitable for use with a container filling machine for detecting the integrity of discrete articles for personal treatment to be loaded in a container, said sensing device comprising:
  a) a pair of capacitor plates positioned in a substantially opposing relationship for creating therebetween an electric field, in response to voltage impressed across the plates which is of less than 100V;
  b) a processing unit in communication with said pair of capacitor plates, said processing unit being operative for:
    i) detecting a change in capacitance as a discrete article for personal treatment passes through said electric field;
    ii) determining the integrity of the discrete article for personal treatment at least in part on the basis of said change in capacitance
    iii) upon a determination that the discrete article for personal treatment is defective, causing the discrete article for personal treatment to be removed from continued travel towards the container.

27. A sensing device as defined in claim 26, wherein said pair of capacitor plates have a voltage of less than 50V.

28. A sensing device as defined in claim 26, wherein said pair of capacitor plates have a voltage of less than 20V.

29. A sensing device as defined in claim 26, wherein said pair of capacitor plates have a voltage of less than 10V.

30. A sensing device as defined in claim 26, wherein said pair of capacitor plates is a first pair of capacitor plates, said sensing device further comprising a second pair of capacitor plates, said first pair of capacitor plates forming a measurement capacitor and said second pair of capacitor plates forming a reference capacitor.

31. A sensing device as defined in claim 30, wherein said measurement capacitor and said reference capacitor each comprise a driven plate and a non-driven plate.

32. A sensing device as defined in claim 31, wherein said measurement capacitor and said reference capacitor share a common non-driven plate.

33. A container filling machine for loading discrete articles for personal treatment into a container, the container filling machine comprising:
 a) a sensing device operative for detecting the integrity of discrete articles for personal treatment to be loaded in the container, the sensing device comprising:
  i) a measurement capacitor;
  ii) a reference capacitor; and
  iii) a processing unit in communication with the measurement capacitor and the reference capacitor for detecting a difference in capacitance change between the measurement capacitor and the reference capacitor as a discrete article for personal treatment passes through the measurement capacitor;
  iv) determining the integrity of the discrete article for personal treatment at least in part on the basis of the difference in capacitance change;
 b) a rejection device for removing the discrete article for personal treatment from continued travel towards the container when the discrete article for personal treatment has been detected by the sensing device as being defective.

34. The container filling machine as defined in claim 33, wherein the processing unit determines the integrity of the discrete article for personal treatment at least in part on the basis of the difference in capacitance change and a characteristic capacitance change signature.

35. The container filling machine as defined in claim 34, wherein the processing unit is operative for deriving the characteristic capacitance change signature at least in part on the basis of capacitance change values that are generated when a plurality of integral discrete articles for personal treatment are passed through the measurement capacitor.

36. The container filling machine as defined in claim 33, wherein the measurement capacitor and the reference capacitor each comprise a driven plate and a non-driven plate.

37. The container filling machine as defined in claim 36, wherein the measurement capacitor and the reference capacitor share a common non-driven plate.

38. The container filling machine as defined in claim 37, wherein the processing unit determines the integrity of the discrete article for personal treatment by comparing the difference in capacitance change with the characteristic capacitance change signature.

39. The container filling machine as defined in claim 33, wherein the measurement capacitor and the reference capacitor have a voltage of less than 50V.

40. A container filling machine for detecting the integrity of discrete articles for personal treatment to be loaded in a container, the container filling machine comprising:
 a) a capacitive sensing device; and
 b) a processing entity operative for:
  i) deriving a characteristic capacitance change signature associated with a given type of discrete article for personal treatment, the characteristic capacitance change signature being derived at least in part on a basis of capacitance measurements obtained by passing a plurality of integrally formed discrete articles for personal treatment of the given type through the capacitive sensing device;
  ii) once the characteristic capacitance change signature has been derived, determining the integrity of a subsequent discrete article for personal treatment belonging to the given type at least in part on a basis of a capacitance measurement obtained for the discrete article for personal treatment belonging to the given type and the characteristic capacitance change signature.

41. The container filling machine as defined in claim 40, wherein the capacitive sensing device comprises:
 i) a measurement capacitor;
 ii) a reference capacitor.
 wherein the processing entity detects a difference in capacitance change between the measurement capacitor and the reference capacitor as the discrete article for personal treatment belonging to the given type passes through the measurement capacitor, and wherein determining the integrity of the discrete article for personal treatment belonging to the given type is done at least in part on the basis of the difference in capacitance change and the characteristic capacitance change signature.

42. The container filling machine as defined in claim 41, wherein determining the integrity of the discrete article for personal treatment belonging to the given type is done by comparing the difference in capacitance change with the characteristic capacitance change signature.

43. The container filling machine as defined in claim 41, further comprising a voltage adjusting circuit for adjusting a voltage supplied to a driven plate of the measurement capacitor in response to a change in voltage at a non-driven plate when the discrete article for personal treatment belonging to the given type passes through the measurement capacitor.

44. The container filling machine as defined in claim 43, wherein the voltage adjusting circuit adjusts the voltage supplied to the driven plate of the measurement capacitor until the voltage at the non-driven plate reaches a predetermined reference voltage.

45. The container filling machine as defined in claim 43, wherein the processing entity determines the difference in capacitance change at least in part on a basis of a voltage adjustment controlled by the voltage adjusting circuit for causing the non-driven plate to reach the predetermined reference voltage.

46. The container filling machine as defined in claim 41, wherein the measurement capacitor and the reference capacitor have a voltage of less than 50V.

47. A method of generating a characteristic capacitance change signature associated with a given type of discrete article for personal treatment, the method comprising:
 a) passing a plurality of integrally formed discrete articles for personal treatment of a given type through a capacitive sensing device that comprises a measurement capacitor and a reference capacitor;

b) obtaining from the capacitive sensing device, a capacitance measurement for each of the plurality of integrally formed discrete articles for personal treatment of the given type;

c) deriving a characteristic capacitance change signature associated with the discrete articles for personal treatment of the given type at least in part on a basis of the capacitance measurements obtained for each of the plurality of integrally formed discrete articles for personal treatment of the given type.

48. A container filling machine for loading discrete articles for personal treatment into a container, the container filling machine comprising:

a) a capacitive sensing device for receiving a plurality of known integrally formed discrete articles for personal treatment of a given type and obtaining a capacitive measurement for each one of the known integrally formed discrete articles for personal treatment of the given type;

b) a processing entity for deriving a characteristic capacitance change signature associated with discrete articles for personal treatment of the given type at least in part on a basis of the capacitance measurements obtained by the capacitive sensing device, the characteristic capacitance change signature being used to determine the integrity of subsequent discrete articles for personal treatment of the given type.

* * * * *